United States Patent
Somoza et al.

(10) Patent No.: US 10,561,633 B2
(45) Date of Patent: Feb. 18, 2020

(54) HYDROXYFLAVANONES AS APPETITE STIMULANTS

(71) Applicant: Symrise AG, Holzminden (DE)

(72) Inventors: Veronika Somoza, Weidling (AT); Barbara Rohm, Vienna (AT); Kathrin Liszt, Vienna (AT); Marc Pignitter, Vienna (AT); Christina Hochkogler, Gänserndorf (AT); Jakob Ley, Holzminden (DE); Sabine Widder, Holzminden (DE); Gerhard Krammer, Holzminden (DE)

(73) Assignee: SYMRISE AG, Holzminden (DE)

( * ) Notice: Subject to any disclaimer, the term of this patent is extended or adjusted under 35 U.S.C. 154(b) by 144 days.

(21) Appl. No.: 15/329,062

(22) PCT Filed: Jul. 26, 2015

(86) PCT No.: PCT/EP2015/067092
§ 371 (c)(1),
(2) Date: Jan. 25, 2017

(87) PCT Pub. No.: WO2016/016153
PCT Pub. Date: Feb. 4, 2016

(65) Prior Publication Data
US 2017/0135982 A1 May 18, 2017

(30) Foreign Application Priority Data
Jul. 30, 2014 (EP) .................................... 14179087

(51) Int. Cl.
| | |
|---|---|
| A61K 31/352 | (2006.01) |
| A23L 33/10 | (2016.01) |
| A23C 23/00 | (2006.01) |
| A23G 3/36 | (2006.01) |
| A23G 4/06 | (2006.01) |
| A23L 2/52 | (2006.01) |
| C07D 311/30 | (2006.01) |

(52) U.S. Cl.
CPC ............ *A61K 31/352* (2013.01); *A23C 23/00* (2013.01); *A23G 3/36* (2013.01); *A23G 4/06* (2013.01); *A23L 2/52* (2013.01); *A23L 33/10* (2016.08); *C07D 311/30* (2013.01); *A23V 2002/00* (2013.01)

(58) Field of Classification Search
CPC .................................................... A61K 31/352
See application file for complete search history.

(56) References Cited

U.S. PATENT DOCUMENTS 5,621,011 A 4/1997 Lafon

FOREIGN PATENT DOCUMENTS

| EP | 1 258 200 A2 | 11/2002 | |
|---|---|---|---|
| EP | 1258200 B1 * | 2/2005 | ............ A23F 3/405 |
| EP | 2 386 211 A1 | 11/2011 | |
| EP | 2 522 346 A1 | 11/2012 | |
| EP | 2 529 633 A1 | 12/2012 | |
| EP | 2 614 727 A1 | 7/2013 | |
| JP | 2008-156297 A | 7/2008 | |
| JP | 2008156297 A * | 7/2008 | |
| KR | 2013-0010192 A | 1/2013 | |

OTHER PUBLICATIONS

"Yerba Santa." (Apr. 10, 2014). Accessed Sep. 13, 2018. Available from: < https://web.archive.org/web/20140410022909/ https://www.herbs2000.com/herbs/herbs_yerba_santa.htm >. (Year: 2014).*
Ley, J.P., et al. ". . . Flavonones from Herba Santa . . .". J. Ag. and Food Chemistry. (2005), vol. 53, pp. 6061-6066. (Year: 2005).*
"Hoja Santa Leaf." (Jun. 23, 2011). Accessed Sep. 17, 2018. Available from: < https://www.oldtribes.com/products/ hoja-santa-leaf >. (Year: 2011).*
Kim et al, "Hesperetin Stimulates Cholecystokinin Secretion in Enteroendocrine STC-1 Cells," Biomol. Ther. 21(2), pp. 121-125 (2013).

* cited by examiner

*Primary Examiner* — Andrew D Kosar
*Assistant Examiner* — John S Kenyon
(74) *Attorney, Agent, or Firm* — Polsinelli PC

(57) ABSTRACT

The invention relates to compounds of formula (I) or the salts thereof, said compounds of formula (I) being selected from among the group consisting of homoeriodictyol (1), eriodictyol (2), hesperetin (3) and sterubin (4), for use in the treatment of an ailment which can be alleviated or prevented by influencing the serotonin level and the concentration of free fatty acids in the blood.

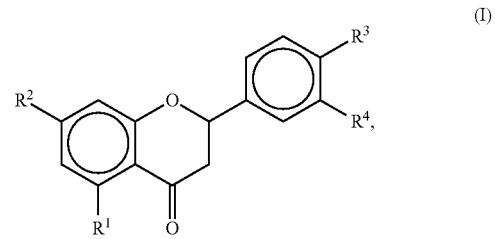

14 Claims, 2 Drawing Sheets

HYDROXYFLAVANONES AS APPETITE STIMULANTS

FIELD OF THE INVENTION

The invention relates to the use of hydroxyflavones of formula (I) or salts thereof as appetite stimulants, preferably in orally consumable products which are selected from the group consisting of foodstuffs (in particular liquid or solid foodstuffs, including semi-finished products), feeds and medicaments (pharmaceutical preparations).

PRIOR ART

Older people often feel a reduced appetite for food, which in extreme cases can even lead to malnutrition. A decreased appetite can have various causes, for example generally reduced sensory sensitivity, fatigue, generalized diseases, the use of medicines, or also unpleasant experiences associated with dryness of the mouth and food consumption. In order to increase the appetite for food, it is possible in general to improve the recipes, for example in respect of color, flavor, taste and also texture. However, it is also conceivable to increase the feeling of appetite by influencing specific hormones or neurotransmitters.

In order to bring about increased consumption of calorifically relevant food constituents, it is desirable to find appetite-increasing substances which are safe, already approved and generally accepted and which are able to increase the feeling of hunger and the natural appetite. It is known that the appetite can be increased by lowering serotonin release in certain areas of the brain with simultaneous exposure to nutrients through the orally consumable products (in particular foodstuffs) that are consumed. An increase in the feeling of hunger is achieved, inter alia, by increased release of the gastrointestinal hunger hormone ghrelin, which is inhibited by a high concentration of free fatty acid in the blood (Gormsen et al. 2006; Eur J Endocrinology). Lowering free fatty acids in the blood thus leads to an increase in appetite and can be brought about by an increased uptake of free fatty acids by peripheral cells (for example adipocytes).

Accordingly, the object of the present invention was to identify substances which are able to influence and reduce or lower in particular the serotonin level and/or the concentration of free fatty acids in the blood, in order to stimulate the appetite. It was part of the present object to identify appetite-stimulating substances which in particular comply with food laws and are thus toxicologically safe to use. It was likewise an object of the present invention to identify appetite-stimulating substances which are easily accessible and, where possible, occur naturally, preferably can be obtained as a plant extract.

BRIEF DESCRIPTION OF THE INVENTION

Implementation of the present technology will now be described, by way of example only, with reference to the attached figures, wherein:

FIG. 1 is a graph showing the amount of serotonin release from neuronal SH-SY5Y cells after incubation with homoeriodictyol in concentrations of 0.001 µM, 0.01 µM, 0.01 µM, 1 µM and 10 µM in accordance with aspects of the disclosure;

FIG. 2 is a schematic representation of the test procedure of the crossover human intervention for determining the change in the serotonin plasma concentration 30 minutes after administration of 125 ml of water (test day 1) or 30 mg of homoeriodictyol dissolved in 125 ml of water (test day 2) according to aspects of the disclosure;

Figure 1:
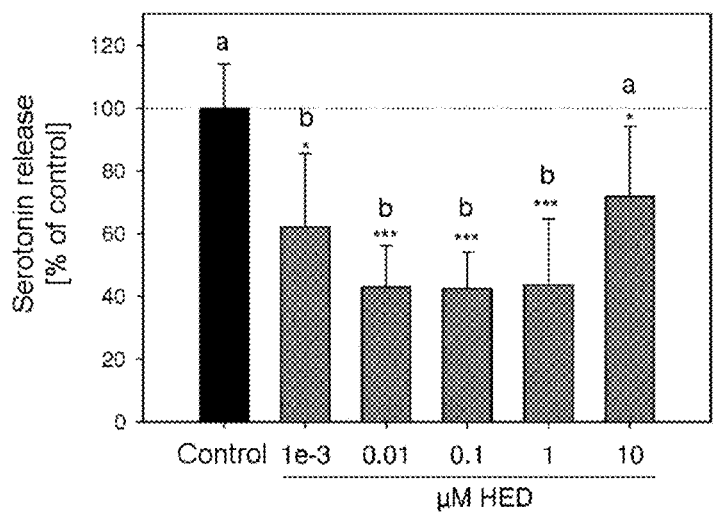

It should be understood that the various aspects of the disclosure are not limited to the arrangements, amounts, compositions, and/or instrumentality shown in the drawings.

DESCRIPTION OF THE INVENTION

A first subject of the invention relates to compounds of formula (I) or salts thereof

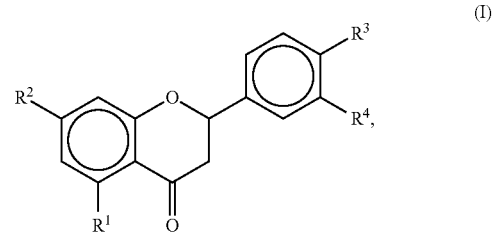

wherein the compounds of formula (I) are selected from the group consisting of: homoeriodictyol (1), eriodictyol (2), hesperetin (3) and sterubin (4), for use in the treatment of a condition which can be alleviated or prevented by influencing the serotonin level and the concentration of free fatty acids in the blood.

In a preferred embodiment of the present invention, the use is preferably directed to compounds of formula (I) which are selected from the group consisting of: homoeriodictyol (1), eriodictyol (2), hesperetin (3) and sterubin (4), wherein the stereocenter at C-2 in each case has the (R) or (S) configuration.

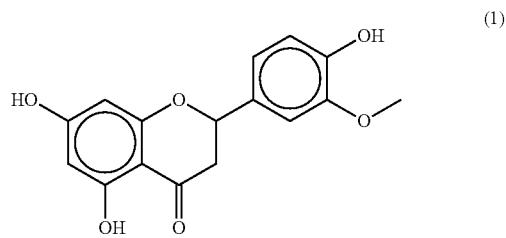

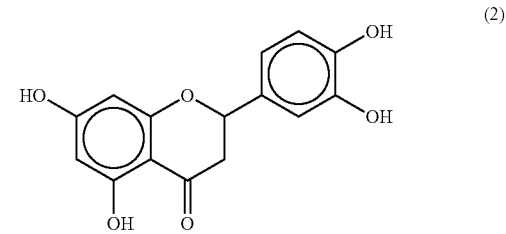

-continued

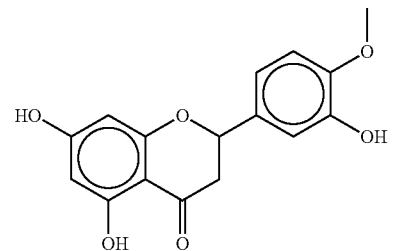

(3)

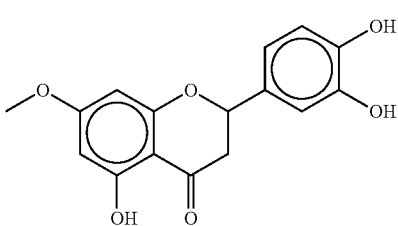

(4)

Preferably, mixtures of both configurations (R) and (S) are used, particularly preferably a mixture enriched in (S) configuration. Compounds of formula (I) are preferably used in the form of (2R) and/or (2S) enantiomers, so that a preferred embodiment is the use of compounds of formula (I) in the form of (2R) and/or (2S) enantiomers.

Compounds of formula (I) are preferably used in the form of their salts, wherein the countercations are selected in a preferred embodiment from the group consisting of: ammonium ions, trialkylammonium ions, sodium, potassium, magnesium or calcium cations. The monosodium salt of compound (1), the homoeriodictyol sodium salt (HEDNa), is particularly preferred.

A further subject of the invention relates to a medicament comprising compounds of formula (I) for use in the treatment of a condition which can be alleviated or prevented by influencing the serotonin level and the concentration of free fatty acids in the blood.

A third subject of the invention relates to compounds of formula (I) or salts thereof

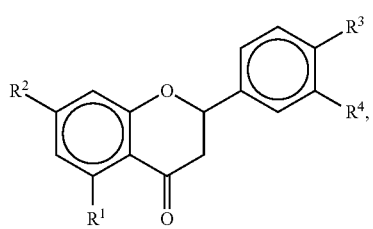

(I)

wherein the compounds of formula (I) are selected from the group consisting of: homoeriodictyol (1), eriodictyol (2), hesperetin (3) and sterubin (4), for use as claimed in claim 1, wherein the condition to be treated is lack of appetite.

A further subject of the invention relates to a substance mixture comprising
(i) at least one compound as claimed in claim 1 or salts thereof,
(ii) at least one solid carrier,
(iii) one or more flavorings,
with the proviso that the sum of components (i), (ii) and (iii), together with any further ingredients, is 100% by weight, based on the total amount of the total substance mixture for use as claimed in claim 1, wherein the condition to be treated is lack of appetite.

Natural sources of and means for obtaining the mentioned hydroxyflavanones of formula (I), in particular compounds (1) to (4), are known in the prior art. For example, the preparation of the mentioned hydroxyflavones is described in EP 1,258,200-B1, EP 1,998,636-B1 or EP 2,017,272 B1. Extracts or isolates from Herba Santa are preferably used, wherein purified homoeriodictyol sodium salt according to EP 1,258,200-B1 or homoeriodictyol-rich fractions as described in EP 2,633,885 are most particularly preferably used for the preparation. Suitable solvents for extraction, in particular for foodstuffs and semi-luxury foods, are water, ethanol, methanol, 1,2-propylene glycol, glycerol, acetone, dichloromethane, acetic acid ethyl ester, diethyl ether, hexane, heptane, triacetin, vegetable oils or fats, supercritical carbon dioxide and mixtures thereof.

Hydroxyflavanones of formula (I) have hitherto been known as taste-modulating flavorings (EP 1,258,200-B1, EP 1,998,636-B1). Their action on the serotonin level and on the concentration of free fatty acids in the blood, in particular in mammals, preferably in humans, has hitherto not been known. The resulting possible use for increasing the appetite has thus likewise hitherto not been known.

Accordingly, a preferred embodiment of the present invention is the use of the compounds of formula (I), in particular compounds (1) to (4) or mixtures thereof, preferably mixtures of the (R) and/or (S) enantiomers, for influencing the serotonin level and the concentration of free fatty acids in the blood in mammals, preferably in humans.

A preferred embodiment of the present invention is likewise the use of the compounds of formula (I), in particular compounds (1) to (4) or mixtures thereof, preferably mixtures of the (R) and/or (S) enantiomers, as compositions for increasing the appetite.

Within the meaning of the present inventions, compounds or hydroxyflavanones of formula (I) are always to be understood as being in particular compounds (1) to (4) or mixtures thereof, preferably mixtures of the (R) and/or (S) enantiomers or salts. It is preferably a mixture of the compounds of formula (I), preferably compounds (1) to (4), enriched in S configuration.

The use of the hydroxyflavanones of formula (I) for stimulating the appetite has nothing to do with their already known taste-improving properties, in particular their bitter-masking action. In contrast to the present invention, the presence of bitter-tasting substances is necessary when these compounds are used as a taste-improving substance, whereas such substances do not necessarily have to be present in the case of the present invention. In particular, it was surprising that the hydroxyflavanones of formula (I), in addition to the activity already known, also have an influence on serotonin release and are able to reduce it both in neuronal cell cultures and in in vivo experiments in blood plasma.

Surprisingly, it has additionally been found that hydroxyflavanones of formula (I)
in a concentration of approximately from 0.001 µM to 10 µM (about 0.03 µg/kg to about 3 mg/kg) are capable of lowering serotonin release by up to 70% compared with the respective control, and also
in a concentration of approximately 0.1 µM are capable of increasing fatty acid uptake in adipocytes by 8% compared with the control.

The concentrations employed for the intended uses according to the invention of the hydroxyflavanones of formula (I) are too low, compared with typical use concentrations (as described in EP 1,258,200-B1, EP 1,998,636-B1), to achieve a pronounced taste effect.

In a preferred embodiment, the compounds of formula (I) or salts thereof are formulated as oral pharmaceutical preparations.

For the application according to the invention, hydroxyflavanones of formula (I) are preferably used in a therapeutic method or in a non-therapeutic use according to the invention, wherein the hydroxyflavanones of formula (I) are used on their own or as a mixture constituent of an orally consumable product, wherein the hydroxyflavanone or the hydroxyflavanones is/are present in a concentration of 30 mg/kg or less, based on the total mass of the orally consumable product, preferably in a concentration of 10 mg/kg or less, particularly preferably in a concentration of 3 mg/kg or less.

An orally consumable product according to the invention is preferably selected from the group consisting of foodstuffs (in particular liquid or solid products, including semi-finished products), feeds and medicaments (pharmaceutical preparations). The hydroxyflavones of formula (I) present invention are suitable in particular for use in cattle feed for the feeding of animals, in particular for influencing the serotonin level and/or the concentration of free fatty acids in the blood and accordingly for increasing the appetite in animals, especially in mammals. Accordingly, a further subject of the invention also includes a medicament comprising compounds of formula (I) more particularly for influencing the serotonin level and/or the concentration of free fatty acids in the blood of mammals.

A further subject of the present invention is the (cosmetic) application of compounds of formula (I) or salts thereof

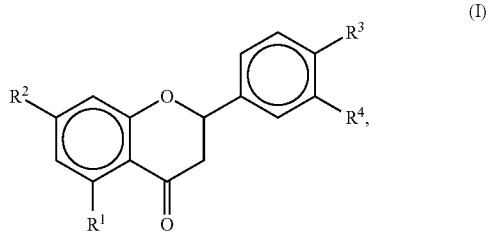

(I)

wherein
$R^1$ represents H or OH,
$R^2$ represents H, OH, or $OCH_3$,
$R^3$ represents H, OH, or $OCH_3$,
and
$R^4$ represents H, OH, or $OCH_3$,
wherein at least two of the radicals $R^1$, $R^2$, $R^3$ and $R^4$
each represent an OH,
in foodstuffs consumed for nourishment or pleasure. The cosmetic application is directed especially to the action of hydroxyflavones of formula (I) as appetite-stimulating substances in cosmetically oriented products which are not pharmaceutical compositions, that is to say are not used for therapeutic purposes.

In the cosmetic application or use there are preferably used compounds of formula (I) or salts thereof wherein
$R^1$ represents OH,
$R^2$ represents OH, or $OCH_3$,
$R^3$ represents OH, or $OCH_3$, and
$R^4$ represents OH, or $OCH_3$,
wherein at least three of the radicals $R^1$, $R^2$, $R^3$ and $R^4$ each represent an OH.

The compounds of formula (I) are preferably selected from the group consisting of: homoeriodictyol (1), eriodictyol (2), hesperetin (3) and sterubin (4) or mixtures thereof, preferably mixtures of the (R) and/or (S) enantiomers, particularly preferably a mixture enriched in S configuration.

A further aspect of the present invention is the non-therapeutic use of the hydroxyflavones of formula (I) for influencing the serotonin level and/or the concentration of free fatty acids in the blood in order to increase the appetite. In the case of the mentioned non-therapeutic application or use, the foodstuff consumed for nourishment or pleasure is preferably an orally consumable product. The non-therapeutic use can be a cosmetic use or application.

A further subject of the present invention is the use of hydroxyflavones of formula (I) or salts thereof as medicaments, preferably for treating lack of appetite or as an appetite stimulant.

Within the scope of the present text, the term "foodstuff" includes a large number of products. The term "foodstuff" includes in particular products as are discussed below in connection with foodstuffs according to the invention.

The term "foodstuff" includes in particular products which are foodstuffs according to REGULATION (EC) No. 178/2002 OF THE EUROPEAN PARLIAMENT AND OF THE COUNCIL of 28 Jan. 2002. According to this regulation, "foodstuffs" are any substances or products which, in the processed, partially processed or unprocessed state, are intended to be or can reasonably be expected to be ingested by humans. "Foodstuffs" also include drinks, chewing gum and also any substances—including water—which are intentionally added to the foodstuff during its manufacture, processing or treatment.

The term "feed" within the scope of the present text includes any form of animal feed. Many of the foodstuffs mentioned hereinbelow can also be used as feeds.

The term "medicament" within the scope of the present text includes substances or substance compositions which are intended as agents having properties of healing or preventing human or animal diseases or which can be used in or on the human or animal body or administered to a human or animal in order either to restore, correct or influence human or animal physiological functions by a pharmacological, immunological or metabolic action or to provide a medical diagnosis. Medicaments can be used in individual cases for non-therapeutic, in particular cosmetic purposes.

It will be appreciated that foodstuffs or feeds can be converted into corresponding medicaments by the addition of substances or substance compositions which are intended as agents having properties of healing or preventing human or animal diseases.

In order to avoid an undesirable increase in the body weight of the consumer as a result of the increased appetite and associated higher consumption, it has been found to be expedient to limit the potential calorific intake and to offer for consumption orally consumable products according to the invention (in particular foodstuffs, feeds or medicaments) which for their part already have a low energy density. Accordingly, a preferred orally consumable product according to the invention (in particular foodstuff, feed and medicament) contains not more than 200 kcal/100 g of the orally consumable product, preferably not more than 100 kcal/100 g, particularly preferably not more than 40 kcal/100 g.

Preferred orally consumable products according to the invention (in particular foodstuffs, feeds or medicaments)

are any preparations or compositions which are suitable for consumption and serve the purpose of nourishment, oral care or pleasure and are generally products which are intended to be introduced into the human or animal oral cavity, to remain there for a certain time and then to be either consumed (e.g. ready-to-eat foodstuffs or feeds, see also below) or removed from the oral cavity again (e.g. chewing gums or oral care products or medicinal mouthwashes). Such products include all substances or products which, in the processed, partially processed or unprocessed state, are intended to be ingested by the human or animal. They also include substances which are added to orally consumable products (in particular foodstuffs, feeds and medicaments) during their manufacture, processing or treatment and are intended to be introduced into the human or animal oral cavity.

The orally consumable products according to the invention (in particular foodstuffs, feeds and medicaments) also include substances which, in the unchanged, prepared or processed state, are intended to be swallowed by the human or animal and then digested; in this respect, the orally consumable products according to the invention also include casings, coatings or other coverings which are intended to be swallowed at the same time as the product or in the case of which swallowing is to be anticipated. The expression "orally consumable product" includes ready-to-eat foodstuffs and feeds, that is to say foodstuffs or feeds whose composition is already complete in terms of the substances that are important for the taste. The expressions "ready-to-eat foodstuff" or "ready-to-eat feed" also include drinks as well as solid or semi-solid ready-to-eat foodstuffs or feeds. There may be mentioned as examples frozen products which must be defrosted and heated to consumption temperature before they are eaten. Products such as yoghurt or ice cream as well as chewing gums or hard caramels also belong to the ready-to-eat foodstuffs or feeds.

Preferred orally consumable products according to the invention (in particular foodstuffs and feeds) also include "semi-finished products". In the context of the present text, a semi-finished product is to be understood as being an orally consumable product which is unsuitable for use as a ready-to-eat orally consumable product (in particular foodstuff or feed) owing to the very high content of flavorings and taste-imparting substances. Only by mixing with at least one further constituent (i.e. by reducing the concentration of the flavorings and taste-imparting substances in question) and optionally further process steps (e.g. heating, freezing) is the semi-finished product converted into a ready-to-eat orally consumable product (in particular foodstuff or feed). Packet soups, extracts for baking and custard powder may be mentioned here as examples of semi-finished products.

Orally consumable products according to the invention (in particular foodstuffs, feeds or medicaments) also include "oral care products". An oral care product (also called oral hygiene product or oral hygiene preparation) within the meaning of the invention is understood as being one of the formulations known to the person skilled in the art for cleaning and caring for the oral cavity and the pharynx and for freshening the breath. Care of the teeth and gums is expressly included here. Administration forms of common oral hygiene formulations are in particular creams, gels, pastes, foams, emulsions, suspensions, aerosols, sprays, as well as capsules, granules, pastilles, tablets, lozenges or chewing gums; this list is not to be interpreted as being limiting for the purposes of this invention.

An orally consumable product according to the invention (in particular foodstuff or feed) preferably comprises one or more preparations which are consumed for nourishment or pleasure. They include in particular (reduced-calorie) baked goods (e.g. bread, dry biscuits, cakes, other baked goods), confectionery (e.g. chocolates, chocolate bar products, other products in bar form, fruit gums, dragées, hard and soft caramels, chewing gum), non-alcoholic drinks (e.g. cocoa, coffee, green tea, black tea, (green, black) tea drinks enriched with (green, black) tea extracts, rooibos tea, other herbal teas, fruit-containing soft drinks, isotonic drinks, refreshment drinks, nectars, fruit and vegetable juices, fruit or vegetable juice preparations), instant drinks (e.g. instant cocoa drinks, instant tea drinks, instant coffee drinks), meat products (e.g. ham, fresh sausage or raw sausage preparations, spiced or marinated fresh or salt meat products), eggs or egg products (dried egg, egg white, egg yolk), cereal products (e.g. breakfast cereals, muesli bars, pre-cooked finished rice products), milk products (e.g. full-fat or reduced-fat or fat-free milk drinks, rice pudding, yoghurt, kefir, fresh cheese, soft cheese, hard cheese, dried milk powder, whey, butter, buttermilk, partially or fully hydrolyzed milk-protein-containing products), products made from soya protein or other soybean fractions (e.g. soya milk and products produced therefrom, drinks containing isolated or enzymatically treated soya protein, soya-flour-containing drinks, soya-lecithin-containing preparations, fermented products such as tofu or tempeh or products made therefrom and mixtures with fruit preparations and optionally flavorings), fruit preparations (e.g. jams, fruit ice, fruit sauces, fruit fillings), vegetable preparations (e.g. ketchup, sauces, dried vegetables, frozen vegetables, pre-cooked vegetables, preserved vegetables), snack articles (e.g. baked or fried potato chips or potato pulp products, corn- or groundnut-based extrudates), products based on fat and oil or emulsions thereof (e.g. mayonnaise, remoulade, dressings, in each case full-fat or reduced-fat), other ready meals and soups (e.g. dried soups, instant soups, pre-cooked soups), spices, spice mixtures and also, in particular, seasonings which are used, for example, in the snacks sector, sweetener preparations, tablets or sachets, other preparations for sweetening or whitening drinks or other foods. The preparations within the meaning of the invention can also be used as semi-finished products for the production of further preparations consumed for nourishment or pleasure. The preparations within the meaning of the invention can also be in the form of capsules, tablets (uncoated and coated tablets, e.g. enteric coatings), dragées, granules, pellets, solid mixtures, dispersions in liquid phases, in the form of emulsions, in the form of powders, in the form of solutions, in the form of pastes or in the form of other swallowable or chewable preparations and in the form of food supplements.

Particular preference is given to reduced-calorie confectionery (e.g. muesli bar products, fruit gums, dragées, hard and soft caramels, chewing gum), non-alcoholic drinks (e.g. cocoa, green tea, black tea, (green, black) tea drinks enriched with (green, black) tea extracts, rooibos tea, other herbal teas, fruit-containing soft drinks, isotonic drinks, refreshment drinks, nectars, fruit and vegetable juices, fruit or vegetable juice preparations), instant drinks (e.g. instant cocoa drinks, instant tea drinks), cereal products (e.g. breakfast cereals, muesli bars, pre-cooked finished rice products), milk products (e.g. full-fat or reduced-fat or fat-free milk drinks, rice pudding, yoghurt, kefir, dried milk powder, whey, buttermilk, partially or fully hydrolyzed milk-protein-containing products), products made from soya protein or other soybean fractions (e.g. soya milk and products produced therefrom, drinks containing isolated or enzymatically treated soya protein, soya-flour-containing drinks, soya-lecithin-containing preparations, fermented products such as tofu or tempeh or products made therefrom and mixtures with fruit preparations and optionally flavorings), sweetener preparations, tablets or sachets, other preparations for sweetening or whitening drinks or other foods.

More particular preference is given to reduced-calorie or calorie-free confectionery (e.g. muesli bar products, fruit gums, dragées, hard caramels, chewing gum), non-alcoholic drinks (e.g. green tea, black tea, (green, black) tea drinks enriched with (green, black) tea extracts, rooibos tea, other herbal teas, fruit-containing low-sugar or sugar-free soft drinks, isotonic drinks, nectars, fruit and vegetable juices, fruit or vegetable juice preparations), instant drinks (e.g. instant (green, black, rooibos, herbal) tea drinks), cereal products (e.g. low-sugar or sugar-free breakfast cereals, muesli bars), milk products (e.g. reduced-fat or fat-free milk drinks, yoghurt, kefir, whey, buttermilk), products made from soya protein or other soybean fractions (e.g. soya milk and products produced therefrom, drinks containing isolated or enzymatically treated soya protein, soya-flour-containing drinks, soya-lecithin-containing preparations, or products made therefrom and mixtures with fruit preparations and optionally flavorings) or sweetener preparations, tablets or sachets.

The preparations can be in the form of capsules, tablets (uncoated and coated tablets, e.g. enteric coatings), dragées, granules, pellets, solid mixtures, dispersions in liquid phases, in the form of emulsions, in the form of powders, in the form of solutions, in the form of pastes or in the form of other swallowable or chewable preparations, for example in the form of food supplements.

The semi-finished products are generally used to produce ready-to-use or ready-to-eat preparations which are consumed for nourishment or pleasure.

Further constituents of a ready-to-eat preparation or semi-finished product consumed for nourishment or pleasure can be base substances, auxiliary substances and additives conventional for foods or semi-luxury foods, for example water, mixtures of fresh or processed, vegetable or animal base or raw substances (e.g. raw, roast, dried, fermented, smoked and/or boiled meat, bone, cartilage, fish, vegetables, herbs, nuts, vegetable juices or pastes or mixtures thereof), digestible or non-digestible carbohydrates (e.g. sucrose, maltose, fructose, glucose, dextrins, amylose, amylopectin, inulin, xylans, cellulose, tagatose), sugar alcohols (e.g. sorbitol, erythritol), natural or hardened fats (e.g. tallow, lard, palm fat, coconut fat, hardened vegetable fat), oils (e.g. sunflower oil, groundnut oil, corn oil, olive oil, fish oil, soybean oil, sesame oil), fatty acids or their salts (e.g. potassium stearate), proteinogenic or non-proteinogenic amino acids and related compounds (e.g. γ-aminobutyric acid, taurine), peptides (e.g. glutathione), natural or processed proteins (e.g. gelatin), enzymes (e.g. peptidases), nucleic acids, nucleotides, taste-correcting agents for unpleasant taste impressions, further taste modulators for further, generally not unpleasant taste impressions, other taste-modulating substances (e.g. inositol phosphate, nucleotides such as guanosine monophosphate, adenosine monophosphate or other substances such as sodium glutamate or 2-phenoxypropionic acid), emulsifiers (e.g. lecithins, diacylglycerols, gum arabic), stabilizers (e.g. carrageenan, alginate), preservatives (e.g. benzoic acid and salts thereof, sorbic acid and salts thereof), antioxidants (e.g. tocopherol, ascorbic acid), chelators (e.g. citric acid), organic or inorganic acidifying agents (e.g. acetic acid, phosphoric acid), additional bitter substances (e.g. quinine, caffeine, limonine, amarogentin, humulones, lupolones, catechols, tannins), substances that prevent enzymatic browning (e.g. sulfite, ascorbic acid), essential oils, plant extracts, natural or synthetic colorings or coloring pigments (e.g. carotinoids, flavonoids, anthocyanins, chlorophyll and derivatives thereof), spices, substances having trigeminal action or plant extracts containing such substances having trigeminal action, synthetic, natural or nature-identical flavorings or fragrances other than those mentioned above, and also odor-correcting agents.

The orally consumable products according to the invention (in particular foodstuffs, feeds and medicaments), for example those in the form of preparations or semi-finished products, preferably comprise a flavoring composition in order to complete and refine the taste and/or odor. A preparation can comprise a solid carrier and a flavoring composition as constituents. Suitable flavoring compositions contain, for example, synthetic, natural or nature-identical flavorings, fragrances and taste-imparting substances, thermal process flavorings, smoke flavorings or other flavor-imparting preparations (e.g. protein [partial] hydrolyzates, preferably protein [partial] hydrolyzates having a high arginine content, grilled flavorings, plant extracts, spices, spice preparations, vegetables and/or vegetable preparations) as well as suitable auxiliary substances and carriers. Particularly suitable here are the flavoring compositions or constituents thereof that produce a roast, meaty (in particular chicken, fish, seafood, beef, pork, lamb, mutton, goat), vegetable-like (in particular tomato, onion, garlic, celery, leek, mushroom, aubergine, seaweed), a spicy (in particular black and white pepper, cardamom, nutmeg, allspice, mustard and mustard products), fried, yeasty, boiled, fatty, salty and/or sharp flavor impression and thus are able to enhance the spicy impression. The flavoring compositions generally contain more than one of the mentioned ingredients.

The energy density of an orally consumable product (in particular foodstuff, feed or medicament) can additionally be lowered by replacing high-energy ingredients of the orally consumable product with substitutes (e.g. low-calorie thickeners instead of fats, low-calorie or calorie-free sweeteners instead of conventional sugars).

Accordingly, in a preferred embodiment, an orally consumable product according to the invention (in particular foodstuff, feed or medicament) comprises (a) one, two or more sweeteners and/or (b) one, two or more thickeners.

The term "sweeteners" here denotes substances having a relative sweetness of at least 25, based on the sweetness of sucrose (which thus has the sweetness value 1). Sweeteners (a) to be used in an orally consumable product according to the invention (in particular foodstuff, feed or medicament) are preferably non-cariogenic and/or have an energy content of not more than 5 kcal per gram of the orally consumable product.

Preference is given according to the invention to an orally consumable product (in particular foodstuff or feed) which comprises milk thickened by lactic acid bacteria and/or cream thickened by lactic acid bacteria and is preferably selected from the group consisting of orally consumable products having a fat content of 4.0% by weight or less, preferably of 1.5% by weight or less, particularly preferably 0.5% by weight or less, in each case based on the total weight of the orally consumable product, and/or is selected from the group consisting of yoghurt, kefir and quark.

Preferably, such an orally consumable product according to the invention (in particular foodstuff or feed) which comprises milk thickened by lactic acid bacteria and/or cream thickened by lactic acid bacteria has an energy content of not more than 150 kcal/100 g of the orally consumable product, preferably not more than 100 kcal/100 g, particularly preferably not more than 75 kcal/100 g, particularly preferably not more than 50 kcal/100 g.

Such an orally consumable product according to the invention (in particular foodstuff or feed) which comprises milk thickened by lactic acid bacteria and/or cream thickened by lactic acid bacteria can further additionally comprise fruits and/or fruit preparations.

In a preferred embodiment, such an orally consumable product (in particular foodstuff or feed) which comprises milk thickened by lactic acid bacteria and/or cream thickened by lactic acid bacteria comprises
sugars and/or
thickeners and/or
gelling agents and/or
sweeteners and/or
flavorings and/or
preservatives.

Within the scope of the present text (unless indicated otherwise or otherwise apparent from the context), "sugars" is the collective term for all sweet-tasting saccharides (mono- and di-saccharides).

Advantageously, an orally consumable product according to the invention (in particular foodstuff or feed) which comprises milk thickened by lactic acid bacteria and/or cream thickened by lactic acid bacteria is an orally consumable product which comprises a probiotic, wherein the probiotic is preferably selected from the group consisting of *Bifidobacterium animalis* subsp. *lactis* BB-12, *Bifidobacterium animalis* subsp. *lactis* DN-173 010, *Bifidobacterium animalis* subsp. *lactis* HN019, *Lactobacillus acidophilus* LA5, *Lactobacillus acidophilus* NCFM, *Lactobacillus johnsonii* La1, *Lactobacillus casei* immunitass/defensis, *Lactobacillus casei* Shirota (DSM 20312), *Lactobacillus casei* CRL431, *Lactobacillus reuteri* (ATCC 55730) and *Lactobacillus rhamnosus* (ATCC 53013).

Particular preference is given to an orally consumable product according to the invention (in particular foodstuff, feed or medicament), wherein the orally consumable product is a drink, wherein the drink preferably has a sugar content of 30 g/100 ml of drink or less, preferably of 15 g/100 ml or less, particularly preferably 5 g/100 ml or less, particularly preferably contains no sugar, and/or wherein the drink contains no ethanol or not more than 0.1 percent by volume ethanol, based on the volume of the drink.

Within the scope of the present invention, orally consumable products according to the invention that are drinks containing ethanol are less preferred.

No ethanol means in the present invention that no ethanol is added and that the preparation contains less than 0.1% by volume, preferably less than 0.01% by volume and particularly preferably no measurable amount of ethanol.

Particular preference is given to orally consumable products according to the invention (in particular foodstuffs, feeds or medicaments) that are a carbonated drink or a non-carbonated drink.

Further aspects of the present invention will become apparent from the following examples and the accompanying claims.

Chewing Gums

The preferred orally consumable products (in particular foodstuffs, feeds or medicaments) can also be chewing gums. Such products typically comprise a water-insoluble component and a water-soluble component.

The chewing gum base is preferably selected from the group consisting of chewing gum or bubble gum bases. The latter are softer, so that chewing gum bubbles can also be formed therewith.

The water-insoluble base, which is also referred to as the "gum base", conventionally comprises natural or synthetic elastomers, resins, fats and oils, plasticizers, fillers, colorings and optionally waxes. The proportion of base in the total composition is usually from 5 to 95, preferably from 10 to 50 and in particular from 20 to 35% by weight. In a typical embodiment of the invention, the base is composed of from 20 to 60% by weight synthetic elastomers, from 0 to 30% by weight natural elastomers, from 5 to 55% by weight plasticizers, from 4 to 35% by weight fillers and, in subordinate amounts, additives such as colorings, antioxidants and the like, with the proviso that they are water-soluble at most in small amounts.

As well as comprising traditionally used natural resins or the natural latex chicle, chewing gum bases which are preferred according to the invention comprise elastomers such as polyvinyl acetates (PVA), polyethylenes, (low- or medium-molecular weight) polyisobutenes (PIB), polybutadienes, isobutene-isoprene copolymers (butyl rubber), polyvinyl ethyl ether (PVE), polyvinyl butyl ether, copolymers of vinyl esters and vinyl ethers, styrene-butadiene copolymers (styrene-butadiene rubber, SBR) or vinyl elastomers, for example based on vinyl acetate/vinyl laurate, vinyl acetate/vinyl stearate or ethylene/vinyl acetate, as well as mixtures of the mentioned elastomers, as described, for example, in EP 0 242 325, U.S. Pat. Nos. 4,518,615, 5,093,136, 5,266,336, 5,601,858 or U.S. Pat. No. 6,986,709.

Suitable synthetic elastomers are, for example, polyisobutylenes having average molecular weights (according to GPC) of from 10,000 to 100,000 and preferably from 50,000 to 80,000, isobutylene-isoprene copolymers ("butyl elastomers"), styrene-butadiene copolymers (styrene:butadiene ratio e.g. 1:3 to 3:1), polyvinyl acetates having average molecular weights (according to GPC) of from 2000 to 90,000 and preferably from 10,000 to 65,000, polyisoprenes, polyethylene, vinyl acetate-vinyl laurate copolymers and mixtures thereof. Examples of suitable natural elastomers are rubbers such as, for example, smoked or liquid latex or guayule as well as natural rubber substances such as jelutong, lechi-caspi, perillo, sorva, massaranduba balata, massaranduba chocolate, nispero, rosindinba, chicle, gutta hang lkang and mixtures thereof. The choice of the synthetic and natural elastomers and the mixing ratios thereof is governed substantially by whether bubbles are to be produced with the chewing gums ("bubble gums") or not. Elastomer mixtures comprising jelutong, chicle, sorva and massaranduba are preferably used.

In most cases, the elastomers are found to be too hard or to have too little deformability during processing, so that it has been found to be advantageous to use concomitantly special plasticizers, which must naturally in particular also satisfy all the requirements for approval as food additives. In this respect, there come into consideration especially esters of resin acids, for example esters of lower aliphatic alcohols or polyols with wholly or partially hardened, monomeric or oligomeric resin acids. In particular, the methyl, glycerol or pentaerythritol esters and mixtures thereof are used for this purpose. Alternatively, there also come into consideration terpene resins, which can be derived from alpha-pinene, beta-pinene, delta-limonene or mixtures thereof.

In addition, chewing gum bases which are preferably to be used according to the invention can preferably comprise further constituents, such as, for example, (mineral) fillers, plasticizers, emulsifiers, antioxidants, waxes, fats or fatty oils, such as, for example, hardened (hydrogenated) vegetable or animal fats, mono-, di- or tri-glycerides. Suitable (mineral) fillers are, for example, calcium carbonate, titanium dioxide, silicon dioxide, talcum, aluminum oxide, dicalcium phosphate, tricalcium phosphate, magnesium hydroxide and mixtures thereof. Suitable plasticizers or agents for preventing sticking (detackifiers) are, for example, lanolin, stearic acid, sodium stearate, ethyl acetate, diacetin (glycerol diacetate), triacetin (glycerol triacetate), triethyl citrate. Suitable waxes are, for example, paraffin waxes, candelilla wax, carnauba wax, microcrystalline waxes and polyethylene waxes. Suitable emulsifiers are, for example, phosphatides such as lecithin, mono- and di-glycerides of fatty acids, for example glycerol monostearate.

Suitable fillers or texturizers are magnesium or calcium carbonate, ground pumice, silicates, especially magnesium or aluminum silicates, clays, aluminum oxides. Talcum, titanium dioxide, mono-, di- and tricalcium phosphate and cellulose polymers.

Suitable emulsifiers are tallow, hardened tallow, hardened or partially hardened vegetable oils, cocoa butter, partial glycerides, lecithin, triacetin and saturated or unsaturated fatty acids having from 6 to 22 and preferably from 12 to 18 carbon atoms and mixtures thereof.

Suitable colorings and whitening agents are, for example, the FD and C types allowed for the coloring of foodstuffs, plant and fruit extracts and titanium dioxide.

The base masses can comprise waxes or be wax-free; examples of wax-free compositions are to be found inter alma in patent specification U.S. Pat. No. 5,286,500, the content of which is expressly incorporated herein by reference.

In addition to the water-insoluble gum base, chewing gum preparations generally comprise a water-soluble component formed, for example, by softeners, sweeteners, fillers, taste-imparting substances, taste enhancers, emulsifiers, colorings, acidifying agents, antioxidants and the like, here with the proviso that the constituents possess at least adequate water solubility. Depending on the water solubility of the specific representatives, individual constituents can accordingly belong both to the water-insoluble phase and to the water-soluble phase. However, it is also possible to use combinations, for example, of a water-soluble and a water-insoluble emulsifier, whereby the individual representatives are then in different phases. The water-insoluble component generally accounts for from 5 to 95 and preferably from 20 to 80% by weight of the preparation.

Water-soluble softeners or plasticizers are added to the chewing gum compositions in order to improve the chewability and the chewing sensation and are present in the mixtures typically in amounts of from 0.5 to 15% by weight. Typical examples are glycerol, lecithin and aqueous solutions of sorbitol, hardened starch hydrolyzates or corn syrup.

Suitable sweeteners are both sugar-containing and sugar-free compounds, which are used in amounts of from 5 to 95, preferably from 20 to 80 and in particular from 30 to 60% by weight, based on the chewing gum composition. Typical saccharide sweeteners are sucrose, dextrose, maltose, dextrin, dried invert sugar, fructose, levulose, galactose, corn syrup and mixtures thereof. Suitable sugar substitutes are sorbitol, mannitol, xylitol, hardened starch hydrolyzates, maltitol and mixtures thereof. There further come into consideration as additives also so-called HIAS (high intensity artificial sweeteners), such as, for example, sucralose, aspartame, acesulfame salts, alitame, saccharin and saccharin salts, cyclamic acid and salts thereof, glycyrrhizins, dihydrochalcones, thaumatin, monellin and the like, on their own or in blends. Particularly effective are also the hydrophobic HIAS which are the subject of international patent application WO 2002 091849 A1 (Wrigleys) and also stevia extracts and the active constituents thereof, in particular ribeaudioside A. The amount of these substances that is used depends especially on their power and is typically in the range of from 0.02 to 8 by weight.

Fillers such as, for example, polydextrose, raftilose, raftiline, fructooligosaccharides (NutraFlora), palatinose oligosaccharides, guar gum hydrolyzates (Sun Fiber) and dextrins are suitable in particular for the production of low-calorie chewing gums.

The choice of further taste-imparting substances is virtually unlimited and is not critical for the nature of the invention. The total content of all taste-imparting substances is usually from 0.1 to 15 and preferably from 0.2 to 5% by weight, based on the chewing gum composition. Suitable further taste-imparting substances are, for example, essential oils, synthetic flavorings and the like, such as, for example, aniseed oil, star anise oil, caraway oil, eucalyptus oil, fennel oil, lemon oil, wintergreen oil, clove oil and the like, as are also used, for example, in oral and tooth care agents.

The chewing gums can further comprise auxiliary substances and additives which are suitable, for example, for tooth care, especially for controlling plaque and gingivitis, such as, for example, chlorhexidine, CPC or triclosan. pH regulators (e.g. buffers or urea), active ingredients against caries (e.g. phosphates or fluorides), biogenic active ingredients (antibodies, enzymes, caffeine, plant extracts) can further be present, provided these substances are allowed for foods and do not interact with one another in an undesirable manner.

Chewing gums according to the invention can generally comprise constituents, such as sugars of various types, sugar substitutes, other sweet-tasting substances, sugar alcohols (in particular sorbitol, xylitol, mannitol), cooling active ingredients, taste-correcting agents for unpleasant taste impressions, further taste-modulating substances (e.g. inositol phosphate, nucleotides such as guanosine monophosphate, adenosine monophosphate or other substances such as sodium glutamate or 2-phenoxypropionic acid), humectants, thickeners, emulsifiers, stabilizers, odor-correcting agents and flavorings (e.g.: eucalyptus-menthol, cherry, strawberry, grapefruit, vanilla, banana, citrus, peach, blackcurrant, tropical fruits, ginger, coffee, cinnamon, combinations (of the mentioned flavorings) with mint flavorings as well as spearmint and peppermint on their own). Of particular interest is inter alia the combination of the flavorings with further substances which have cooling, warming and/or mouthwatering properties.

Ingredients for the Preparations

The foodstuffs, feeds, pharmaceutical preparations and orally consumable preparations of the present invention can comprise further ingredients, such as, for example, sweeteners, food acids, acidity regulators, thickeners and in particular flavorings which can be used both in the foodstuffs sector and in pharmaceutical preparations, so that no rigid line can be drawn here between ingredient lists B and C. Accordingly, the ingredients are used expediently according to the application and use.

Sweeteners

Advantageous sweeteners in a preferred orally consumable product according to the invention (in particular foodstuff, feed or medicament) are selected from the following groups (a1) and (a2):

(a1) naturally occurring sweeteners, preferably selected from the group consisting of (a1-1) miraculin, monellin, mabinlin, thaumatin, curculin, brazzein, pentaidin, D-phenylalanine, D-tryptophan, and extracts or fractions obtained from natural sources containing these amino acids and/or proteins, and the physiologically acceptable salts of these amino acids and/or proteins, in particular the sodium, potassium, calcium or ammonium salts;

(a1-2) neohesperidin dihydrochalcone, naringin dihydrochalcone, stevioside, steviolbioside, rebau-diosides, particularly rebaudioside A, rebaudioside B, rebaudioside C, rebaudioside D, rebaudioside E, rebaudioside F, rebaudioside G, rebaudioside H, dulcosides and rubusoside, suavioside A, suavioside B, suavioside G, suavioside H, suavioside I, suavioside J, baiyunoside 1, baiyunoside 2, phlomisoside 1, phlomisoside 2, phlomisoside 3 and phlomisoside 4, abrusoside A, abrusoside B, abrusoside C, abrusoside D, cyclocaryoside A and cyclocaryoside I, oslandin, polypodoside A, strogin 1, strogin 2, strogin 4, selligueanin A, dihydroquercetin-3-acetate, perillartine, telosmoside A15, periandrin I-V, pterocaryosides, cyclocaryosides, mukurozio-sides, trans-anethole, trans-cinnamaldehyde, bryosides, bryonosides, bryonodulcosides, carnosiflosides, scandenosides, gypenosides, trilobatin, phloridzin, dihydroflavanols, hematoxylin, cyanine, chlorogenic acid, albiziasaponin, telosmosides, gaudichaudioside, mogrosides, mogroside V, hernandulcins, monatin, phyllodulcin, glycyrrhetinic acid and derivatives thereof, in particular glycosides thereof such as glycyrrhizin, and the physiologically acceptable salts of these compounds, in particular the sodium, potassium, calcium or ammonium salts;

(a1-3) extracts or enriched fractions of extracts, selected from the group consisting of Thaumatococcus extracts (katemfe bush), extracts from *Stevia* ssp. (in particular *Stevia rebaudiana*), swingle extracts (*Momordica* or *Siratia grosvenorii*, Luo-Han-Guo), extracts from *Glycerrhyzia* ssp. (in particular *Glycerrhyzia glabra*), extracts from *Rubus* ssp. (in particular *Rubus suavissimus*), citrus extracts and extracts from *Lippia dulcis;*

(a2) synthetic sweet-tasting substances, preferably selected from the group consisting of magap, sodium cyclamate or other physiologically acceptable salts of cyclamic acid, acesulfame K or other physiologically acceptable salts of acesulfame, neohesperidin dihydrochalcone, naringin dihydrochalcone, saccharin, saccharin-sodium salt, aspartame, superaspartame, neotame, alitame, advantame, perillartine, sucralose, lugduname, carrelame, sucrononate and sucrooctate.

Acidity Regulators

Acidity regulators are foodstuff additives which keep the degree of acidity or the basicity, and accordingly the desired pH, of a foodstuff constant. They are mostly organic acids and salts thereof, carbonates, more rarely also inorganic acids and salts thereof. The addition of an acidity regulator partly increases the stability and firmness of the foodstuff, effects a desired precipitation and improves the action of preservatives. Unlike acidifying agents, they are not used to change the taste of foodstuffs. Their action is based on the formation of a buffer system in the foodstuff, in which the pH does not change or changes only slightly upon addition of acidic or basic substances. Examples are:

Acids within the meaning of the invention are preferably acids allowed in foodstuffs, in particular those mentioned here:

E 270—lactic acid
E 290—carbon dioxide
E 296—malic acid
E 297—fumaric acid
E 331—sodium citrate
E 332—potassium citrate
E 333—calcium citrate
E 335—sodium tartrate
E 336—potassium tartrate
E 337—sodium-potassium tartrate
E 338—phosphoric acid
E 353—metatartaric acid
E 354—calcium tartrate
E 363—succinic acid
E 380—triammonium citrate
E 513—sulfuric acid
E 575—glucono-delta-lactone
E 170—calcium carbonate
E 260-263 acetic acid and acetates
E 325-327 lactates (lactic acid)
E 330-333 citric acid and citrates
E 334-337 tartaric acid and tartrates
E 339-341 orthophosphates
E 350-352 malates (malic acid)
E 450-452 di-, tri- and poly-phosphates
E 500-504 carbonates (carbonic acid)
E 507—hydrochloric acid and chlorides
E 513-517 sulfuric acid and sulfates
E 524-528 hydroxides
E 529-530 oxides
E 355-357 adipic acid and adipates
E 574-578 gluconic acid and gluconates Thickeners Thickeners are substances which primarily are capable of binding water. By removing unbound water, the viscosity is increased. Above a concentration that is characteristic for each thickener, networking effects also occur in this respect, which lead to a mostly disproportional increase in the viscosity. In this case, molecules are said to "communicate" with one another, that is to say become entangled. Most thickeners are linear or branched macromolecules (e.g. polysaccharides or proteins), which are able to interact with one another through intermolecular interactions, such as hydrogen bridges, hydrophobic interactions or ionic bonds. Extreme cases of thickening agents are phyllosilicates (bentonite, hectorite) or hydrated $SiO_2$ particles, which are present in disperse form as particles and are able to bind water in their solid-like structure or interact with one another owing to the described interactions. Examples are:

E 400—alginic acid
E 401—sodium alginate
E 402—potassium alginate
E 403—ammonium alginate
E 404—calcium alginate
E 405—propylene glycol alginate
E 406—agar agar
E 407—carrageenan, furcelleran
E 407—locust bean gum
E 412—guar gum
E 413—tragacanth
E 414—gum arabic
E 415—xanthan gum
E 416—karaya gum (Indian tragacanth)
E 417—tara gum (Peruvian locust bean gum)
E 418—gellan gum
E 440—pectin, Opekta
E 440ii—amidated pectin
E 460—microcrystalline cellulose, cellulose powder
E 461—methylcellulose
E 462—ethylcellulose
E 463—hydroxypropylcellulose
E 465—methylethylcellulose
E 466—carboxymethylcellulose, sodium carboxymethylcellulose Flavorings Suitable flavorings are preferably a sensorially active component and are preferably used in a concentration which is greater than its detection threshold. Preferred flavorings which can be part of the substance mixture are to be found, for example, in H. Surburg, J. Panten, Common Fragrance and Flavor Materials, 5th. Ed., Wiley-VCH, Weinheim 2006.

The flavorings can be used in the form of flavoring compositions, which in turn can be used in the form of thermal process flavorings (Maillard products) and/or extracts or ethereal oils of plants or plant parts or fractions thereof.

The foodstuffs or pharmaceutical preparations according to the invention of the present invention can comprise one or more flavorings. Typical examples include: acetophenone, allyl caproate, alpha-ionone, beta-ionone, anisaldehyde, anisyl acetate, anisyl formate, benzaldehyde, benzothiazole, benzyl acetate, benzyl alcohol, benzyl benzoate, beta-ionone, butyl butyrate, butyl caproate, butylidenephthalide, carvone, camphene, caryophyllene, cineole, cinnamyl acetate, citral, citronellol, citronellal, citronellyl acetate, cyclohexyl acetate, cymol, damascone, decalactone, dihydrocoumarin, dimethyl anthranilate, dimethyl anthranilate, dodecalactone, ethoxyethyl acetate, ethyl butyric acid, ethyl butyrate, ethyl caprinate, ethyl caproate, ethyl crotonate, ethyl furaneol, ethyl guaiacol, ethyl isobutyrate, ethyl isovalerate, ethyl lactate, ethyl methylbutyrate, ethyl propionate, eucalyptol, eugenol, ethyl heptylate, 4-(p-hydroxyphenyl)-2-butanone, gamma-decalactone, geraniol, geranyl acetate, geranyl acetate, grapefruit aldehyde, methyl dihydrojasmonate (e.g. Hedion®), heliotropin, 2-heptanone, 3-heptanone, 4-heptanone, trans-2-heptenal, cis-4-heptenal, trans-2-hexenal, cis-3-hexenol, trans-2-hexenoic acid, trans-3-hexenoic acid, cis-2-hexenyl acetate, cis-3-hexenyl acetate, cis-3-hexenyl caproate, trans-2-hexenyl caproate, cis-3-hexenyl formate, cis-2-hexyl acetate, cis-3-hexyl acetate, trans-2-hexyl acetate, cis-3-hexyl formate, para-hydroxybenzyl acetone, isoamyl alcohol, isoamyl isovalerate, isobutyl butyrate, isobutyraldehyde, isoeugenol methyl ether, isopropyl methylthiazole, lauric acid, leavulinic acid, linalool, linalool oxide, linalyl acetate, menthol, menthofuran, methyl anthranilate, methylbutanol, methylbutyric acid, 2-methylbutyl acetate, methyl caproate, methyl cinnamate, 5-methylfurfural, 3,2,2-methylcyclopentenolone, 6,5, 2-methyl heptenone, methyl dihydrojasmonate, methyl jasmonate, 2-methyl methylbutyrate, 2-methyl-2-pentenoic acid, methyl thiobutyrate, 3,1-methylthio hexanol, 3-methylthio hexyl acetate, nerol, neryl acetate, trans,trans-2,4-nonadienal, 2,4-nonadienol, 2,6-nonadienol, 2,4-nonadienol, nootkatone, delta octalactone, gamma octalactone, 2-octanol, 3-octanol, 1,3-octenol, 1-octyl acetate, 3-octyl acetate, palmitic acid, paraldehyde, phellandrene, pentanedione, phenylethyl acetate, phenylethyl alcohol, phenylethyl alcohol, phenylethyl isovalerate, piperonal, propionaldehyde, propyl butyrate, pulegone, pulegol, sinensal, sulfurol, terpinene, terpineol, terpinolene, 8,3-thiomenthanone, 4,4,2-thiomethylpentanone, thymol, delta-undecalactone, gamma-undecalactone, valencene, valeric acid, vanillin, acetoin, ethylvanillin, ethyl vanillin isobutyrate (=3-ethoxy-4-isobutyryloxybenzaldehyde), 2,5-dimethyl-4-hydroxy-3(2H)-furanone and derivatives thereof (preferably homofuraneol (=2-ethyl-4-hydroxy-5-methyl-3(2H)-furanone), homofuronol (=2-ethyl-5-methyl-4-hydroxy-3(2H)-furanone and 5-ethyl-2-methyl-4-hydroxy-3(2H)-furanone), maltol and maltol derivatives (preferably ethyl maltol), coumarin and coumarin derivatives, gamma-lactones (preferably gamma-undecalactone, gamma-nonalactone, gamma-decalactone), delta-lactones (here preferably 4-methyl delta-decalactone, massoilactone, delta-decalactone, tuberolactone), methyl sorbate, divanillin, 4-hydroxy-2(or 5)-ethyl-5(or 2)-methyl-3(2H)furanone, 2-hydroxy-3-methyl-2-cyclopentenone, 3-hydroxy-4,5-dimethyl-2(5H)-furanone, acetic acid isoamyl ester, butyric acid ethyl ester, butyric acid n-butyl ester, butyric acid isoamyl ester, 3-methyl-butyric acid ethyl ester, n-hexanoic acid ethyl ester, n-hexanoic acid allyl ester, n-hexanoic acid n-butyl ester, n-octanoic acid ethyl ester, ethyl 3-methyl-3-phenyl-glycidate, ethyl 2-trans-4-cis-decadienoate, 4-(p-hydroxyphenyl)-2-butanone, 1,1-dimethoxy-2,2,5-trimethyl-4-hexane, 2,6-dimethyl-5-hepten-1-al and phenylacetaldehyde, 2-methyl-3-(methyl-thio)furan, 2-methyl-3-furanthiol, bis(2-methyl-3-furyl)disulfide, furfuryl mercaptan, methional, 2-acetyl-2-thiazoline, 3-mercapto-2-pentanone, 2,5-dimethyl-3-furanthiol, 2,4,5-trimethylthiazole, 2-acetylthiazole, 2,4-dimethyl-5-ethylthiazole, 2-acetyl-1-pyrroline, 2-methyl-3-ethylpyrazine, 2-ethyl-3,5-dimethylpyrazine, 2-ethyl-3,6-dimethylpyrazine, 2,3-diethyl-5-methylpyrazine, 3-isopropyl-2-methoxypyrazine, 3-isobutyl-2-methoxypyrazine, 2-acetyl-pyrazine, 2-pentylpyridine, (E,E)-2,4-decadienal, (E,E)-2,4-nonadienal, (E)-2-octenal, (E)-2-nonenal, 2-undecenal, 12-methyl tridecanal, 1-penten-3-one, 4-hydroxy-2,5-dimethyl-3(2H)-furanone, guaiacol, 3-hydroxy-4,5-dimethyl-2(5H)-furanone, 3-hydroxy-4-methyl-5-ethyl-2(5H)-furanone, cinnamaldehyde, cinnamyl alcohol, methyl salicylate, isopulegol and (not explicitly mentioned here) stereoisomers, enantiomers, position isomers, diastereoisomers, cis/trans-isomers and epimers of these substances.

Vitamins

In a further embodiment of the present invention, foodstuffs or pharmaceutical preparations can comprise a further optional group of additives, vitamins. Vitamins have a very wide variety of different biochemical modes of action. Some act similarly to hormones and regulate the mineral metabolism (e.g. vitamin D) or act on the growth of cells and tissue as well as on cell differentiation (e.g. some forms of vitamin A). Others are antioxidants (e.g. vitamin E and, under some circumstances, also vitamin C). The largest number of vitamins (e.g. the B vitamins) are precursors for enzymatic co-factors which assist enzymes in catalyzing specific processes in the metabolism. In this connection, the vitamin can sometimes be closely bonded to the enzymes, for example as part of the prosthetic group: an example thereof is biotin, which is part of the enzyme responsible for the synthesis of fatty acids. On the other hand, vitamins can also be bonded less strongly and then act as co-catalysts, for example as groups which can readily be removed and transport chemical groups or electrons between the molecules. Folic acid, for example, thus transports methyl, formyl and methylene groups into the cell. Although their assistance in enzyme-substrate reactions is well known, their other properties are also of great importance for the body.

Within the context of the present invention, there come into consideration as vitamins substances which are selected from the group consisting of vitamin A (retinol, retinal, betacarotene),
vitamin $B_1$ (thiamine),
vitamin $B_2$ (riboflavin),
vitamin $B_3$ (niacin, niacinamide),
vitamin $B_5$ (pantothenic acid),
vitamin $B_5$ (pyridoxine, pyridoxamine, paridoxal),
vitamin $B_7$ (biotin),
vitamin $B_9$ (folic acid, folinic acid), vitamin B$_{12}$ (cyanobalamin, hydroxycobalmin, methylcobalmin),
vitamin C (ascorbic acid),
vitamin D (cholecalciferol),
vitamin E (tocopherols, tocotrienols) and
vitamin K (phylloquinone, menaquinone).

The preferred vitamins, in addition to ascorbic acid, are the group of the tocopherols.

Prebiotic Substances

In a further embodiment of the invention, foodstuffs or pharmaceutical preparations of the present invention can further comprise prebiotic substances ("prebiotics"), which form group H. Prebiotics are defined as non-digestible food constituents, the administration of which stimulates the growth or the activity of a number of beneficial bacteria in the large intestine. The addition of prebiotic compounds improves the stability of the anthocyanins against degradation processes in the intestinal tract. In the following are various substances, in particular carbohydrates, which are particularly preferred as prebiotics within the meaning of the invention.

Fructooligosaccharides.

Fructooligosaccharides, or FOS for short, include in particular short-chained representatives having from 3 to 5 carbon atoms, such as, for example, D-fructose and D-glucose. FOS, also referred to as Neosugar, are produced commercially on the basis of sucrose and the enzyme fructosyltransferase, which is obtained from fungi. FOS support in particular the growth of bifidobacteria in the intestine and are marketed especially in the USA in various functionalized foods together with probiotic bacteria.

Inulins.

Inulins belong to a group of naturally occurring oligosaccharides containing fructose. They belong to a class of carbohydrates which are referred to as fructans. They are obtained from the roots of the chicory plant (*Cichorium intybus*) or so-called Jerusalem artichokes. Inulins consist predominantly of fructose units and typically have a glucose unit as end group. The fructose units are linked together via a beta-(2-1)glycosidic bond. The mean degree of polymerization of inulins used as prebiotics in the food sector is from 10 to 12. Inulins likewise stimulate the growth of bifidobacteria in the large intestine.

Isomaltooligosaccharides.

This group is a mixture of alpha-D-linked glucose oligomers, including isomaltose, panose, isomaltotetraose, isomaltopentaose, nigerose, kojibiose, isopanose and higher branched oligosaccharides. Isomaltooligosaccharides are produced by various enzymatic routes. They likewise stimulate the growth of bifidobacteria and lactobacilli in the large intestine. Isomaltooligosaccharides are used especially in Japan as food additives in functionalized foodstuffs. In the meantime they are also becoming established in the USA.

Lactilol.

Lactilol is the disaccharide of lactulose. It is used medically against constipation and in hepatic encephalopathy. In Japan, lactilol is used as a prebiotic. It resists breakdown in the upper intestinal tract but is fermented by various intestinal bacteria, which leads to an increase in bifidobacteria and lactobacilli in the biomass in the intestine. Lactilol is also known by the chemical name 4-0-(beta-D-galactopyranosyl)-D-glucitol. The medical field of application of lactilol in the USA is limited because of a lack of studies; in Europe it is preferably used as a sweetener.

Lactosucrose.

Lactosucrose is a trisaccharide which is composed of D-galactose, D-glucose and D-fructose. Lactosucrose is produced by enzymatic transfer of the galactosyl residue in lactose to sucrose. It is not broken down in either the stomach or the upper part of the intestinal tract and is consumed solely by bifidobacteria for growth. From a physiological point of view, lactosucrose acts as a stimulator for the growth of intestinal flora. Lactosucrose is also known as 4G-beta-D-galactosucrose. It is widely used in Japan as a food additive and as a constituent of functionalized foodstuffs, in particular also as an additive for yoghurts. Lactosucrose is currently also being tested in the USA for a similar intended use.

Lactulose.

Lactulose is a semi-synthetic disaccharide of D-lactose and D-fructose. The sugars are linked via a beta-glycosidic bond, which makes them resistant to hydrolysis by digestive enzymes. Instead, lactulose is fermented by a limited number of intestinal bacteria, which leads to growth in particular of lactobacilli and bifidobacteria. In the USA, lactulose is a medicament against constipation and hepatic encephalopathy which is only available by prescription. In Japan, on the other hand, it is freely sold as a food additive and constituent of functionalized foodstuffs.

Pyrodextrins.

Pyrodextrins comprise a mixture of glucose-containing oligosaccharides, which are formed in the hydrolysis of starch. Pyrodextrins promote the proliferation of bifidobacteria in the large intestine. They too are not broken down in the upper intestinal region.

Soybean Oligosaccharides.

The oligosaccharides of this group are to be found essentially only in soybeans and also in other beans as well as peas. The two leading representatives are the trisaccharide raffinose and the tetrasaccharide stachyose. Raffinose is composed of one molecule of each of D-galactose, D-glucose and D-fructose. Stachyose is composed of two D-galactose molecules and one molecule of each of D-glucose and D-fructose. Soybean oligosaccharides stimulate the growth of bifidobacteria in the large intestine and are already in use in Japan as food additives and in functionalized foodstuffs. In the USA, they are currently being tested for this application.

Transgalactooligosaccharides.

Transgalactooligosaccharides (TOS) are mixtures of oligosaccharides based on D-glucose and D-galactose. TOS are produced from *Aspergillus oryzae* starting from D-lactose with the aid of the enzyme betaglucosidase. Like many other prebiotics, TOS are also stable in the small intestine and stimulate the growth of bifidobacteria in the large intestine. TOS are already being marketed in Europe and also in Japan as food additives.

Xylooligosaccharides.

Xylooligosaccharides contain beta-1,4-linked xylose units. The degree of polymerization of the xylooligosaccharides is between 2 and 4. They are obtained by enzymatic hydrolysis of the polysaccharide xylan. They are already being marketed in Japan as food additives; in the USA, they are still in the test phase.

Biopolymers.

Suitable biopolymers which likewise come into consideration as prebiotics, such as, for example, beta-glucans, are distinguished in that they are produced on the basis of plants; suitable raw material sources are, for example, cereals such as oats and barley, but also fungi, yeasts and bacteria. Also suitable are microbially produced cell wall suspensions or whole cells with a high beta-glucan content. Residual proportions of monomers have 1-3 and 1-4 or 1-3 and 1-6 linkages, whereby the content can vary greatly. Beta-glucans based on yeasts, in particular *Saccharomyces*, especially *Saccharomyces cerevisiae*, are preferably obtained. Other suitable biopolymers are chitin and chitin derivatives, in particular oligoglucosamine and chitosan, which is a typical hydrocolloid.

Galactooligosaccharides (GOS).

Galactooligosaccharides are produced by the enzymatic conversion of lactose, a component of cow's milk. GOS generally comprise a chain of galactose units which are formed by successive transgalactosylation reactions and have a terminal glucose unit. Terminal glucose units are mostly formed by premature hydrolysis of GOS. The degree of polymerization of the GOS can vary quite widely and ranges from 2 to 8 monomer units. A number of factors determine the synthesis and the sequence of the monomer units: the enzyme source, the starting material (lactose concentration and source of the lactose), the enzymes involved in the process, conditions during processing and the composition of the medium.

Probiotic Microorganisms

Probiotic microorganisms, also referred to as "probiotics", are live microorganisms which have beneficial properties for the host. According to the FAO/WHO definition, they are "live microorganisms which, when administered in adequate amounts, confer a health benefit on the host". Lactic acid bacteria (LAB) and bifidobacteria are the most well known probiotics; however, various yeasts and bacilli can also be used. Probiotics are usually consumed as a constituent of fermented foods to which special live cultures have been added, such as, for example, yoghurt, soya yoghurt or other probiotic foods. In addition, tablets, capsules, powders and sachets which contain the microorganisms in freeze-dried form are available. Table A gives an overview of commercially available probiotics and the associated health benefits which can be used within the meaning of the present invention.

TABLE A

| Probiotic substances | | | |
|---|---|---|---|
| Strain | Name | Manufacturer | Benefit |
| *Bacillus coagulans* GBI-30, 6086 | GanedenBC | Ganeden Biotech | Increases the immune response in the case of viral infection |
| *Bifidobacterium animalis* subsp. *lactis* BB-12 | Probio-Tec Bifidobacterium BB-12 | Chr. Hansen | Clinical studies in humans have shown that BB-12 alone or in combination has a positive influence on the gastrointestinal system. |
| *Bifidobacterium infantis* 35624 | Align | Procter & Gamble | A preliminary study has shown that the bacterium can reduce abdominal pain. |
| *Lactobacillus acidophilus* NCFM | | Danisco | A study shows that the side-effects of antibiotic treatments are reduced |
| *Lactobacillus paracasei* St11 (or NCC2461) | | | |

TABLE A-continued

| Probiotic substances | | | |
|---|---|---|---|
| Strain | Name | Manufacturer | Benefit |
| *Lactobacillus johnsonii* La1 (=*Lactobacillus* LC1, *Lactobacillus johnsonii* NCC533) | | Nestlé | Reduces gastritis pain and reduces inflammation |
| *Lactobacillus plantarum* 299v | GoodBelly/ ProViva/ ProbiMage | Probi | Might improve IBS symptoms; however, further studies are required. |
| *Lactobacillus reuteri* American Type Culture Collecton (ATCC)55730 (*Lactobacillus reuteri* SD2112) *Lactobacillus reuteri* Protectis (DSM 17938, daughter strain of ATCC 55730) | | BioGaia | First signs of activity against gingivitis, fever in children and reduction in days of illness in adults. |
| *Saccharomyces boulardii* | DiarSafe and others | Wren Laboratories | Limited evidence in the treatment of acute diarrheal diseases. |
| *Lactobacillus rhamnosus* GR-1 & *Lactobacillus reuteri* RC-14 | Bion Flore Intime/ Jarrow Fem-Dophilus | Chr. Hansen | In a study, evidence of activity against vaginitis. |
| *Lactobacillus acidophilus* NCFM & *Bifidobacterium bifidum* BB-12 | Florajen3 | American Lifeline, Inc | First indications of effectiveness against CDAD |
| *Lactobacillus acidophilus* CL1285 & *Lactobacillus casei* LBC80R | Bio-K+ CL1285 | Bio-K+ International | Indications of improvement in digestion, especially in respect of lactose intolerance. |
| *Lactobacillus plantarum* HEAL 9 & *Lactobacillus paracasei* 8700:2 | Bravo Friscus/ ProbiFrisk | Probi | Tests are currently being carried out on effectiveness against colds. |

Two further forms of lactic acid bacteria which can likewise be used as probiotics are mentioned hereinbelow:

*Lactobacillus bulgaricus;*

*Streptococcus thermophilus.*

Special fermented products based on such lactic acid bacteria can also be used:

mixed pickles fermented bean paste such as tempeh, miso and doenjang;

kefir;

buttermilk;

kimchi;

pao cai;

soy sauce;

zha cai.

Taste Enhancers and Flavorings

The foodstuffs or pharmaceutical preparations of the present invention can further comprise additional flavorings for enhancing a salty, optionally slightly acidic and/or umami taste impression. Preference is given here to compounds having a salty taste and salt-enhancing compounds. Preferred compounds are disclosed in WO 2007/045566.

Also preferred are umami compounds as described in WO 2008/046895 and EP 1 989 944.

Foodstuffs or pharmaceutical preparations of the present invention can further also comprise flavorings for masking bitter and/or astringent taste impressions (taste-correcting agents). The (further) taste-correcting agents are selected, for example, from the following list: nucleotides (e.g. adenosine 5'-monophosphate, cytidine 5'-monophosphate) or pharmaceutically acceptable salts thereof, lactisole, sodium salts (e.g. sodium chloride, sodium lactate, sodium citrate, sodium acetate, sodium gluconate), further hydroxyflavanones (e.g. eriodictyol, homoeriodictyol or sodium salts thereof), in particular according to US 2002/0188019, hydroxybenzoic acid amides according to DE 10 2004 041 496 (e.g. 2,4-dihydroxybenzoic acid vanillylamide, 2,4-dihydroxybenzoic acid N-(4-hydroxy-3-methoxybenzyl)amide, 2,4,6-trihydroxybenzoic acid N-(4-hydroxy-3-methoxybenzyl)-amide, 2-hydroxybenzoic acid N-4-(hydroxy-3-methoxy-benzyl)amide, 4-hydroxybenzoic acid N-(4-hydroxy-3-methoxybenzyl)amide, 2,4-dihydroxybenzoic acid N-(4-hydroxy-3-methoxybenzyl)amide monosodium salt, 2,4-dihydroxybenzoic acid N-2-(4-hydroxy-3-methoxyphenyl)-ethylamide, 2,4-dihydroxybenzoic acid N-(4-hydroxy-3-ethoxybenzyl)amide, 2,4-dihydroxybenzoic acid N-(3,4-dihydroxybenzyl)amide and 2-hydroxy-5-methoxy-N-[2-(4-hydroxy-3-methoxyphenyl)ethyl]amide (aduncamide), 4-hydroxybenzoic acid vanillylamide), bitter-masking hydroxydeoxybenzoins, for example according to WO 2006/106023 (e.g. 2-(4-hydroxy-3-methoxyphenyl)-1-(2,4,6-trihydroxyphenyl)ethanone, 1-(2,4-dihydroxyphenyl)-2-(4-hydroxy-3-methoxyphenyl)ethanone, 1-(2-hydroxy-4-methoxyphenyl)-2-(4-hydroxy-3-methoxyphenyl)-ethanone, amino acids (e.g. gamma-aminobutyric acid according to WO 2005/096841 for reducing or masking an unpleasant taste impression such as bitterness), malic acid glycosides according to WO 2006/003107, mixtures having a salty taste according to PCT/EP 2006/067120, diacetyl trimers according to WO 2006/058893, mixtures of whey proteins with lecithins and/or bitter-masking substances such as ginger diones according to WO 2007/003527, 4-hydroxydihydrochalcones according to EP 1,972,203, dihydrochalcones according to EP 2,353,403, alkamides such as pellitorine according to EP 2,058,297, hydroxyflavanes according to EP 2,253,226, Rubus suavissimus extracts according to EP 2,386,211, vanillyl lignans according to EP 2,517,574, neoisoflavonoids according to EP 2,570,035, decadienoylamino acids according to EP 2,597,082 or heterocyclic neoflavonoids according to EP 2,725,026.

Preferred flavorings are those which cause a sweet odor impression, wherein the further flavoring or flavorings which cause a sweet odor impression are preferably selected from the group consisting of:
vanillin, ethyl vanillin, ethyl vanillin isobutyrate (=3-ethoxy-4-isobutyryloxybenzaldehyde), furaneol (2,5-dimethyl-4-hydroxy-3(2H)-furanone) and derivatives (e.g. homofuraneol, 2-ethyl-4-hydroxy-5-methyl-3(2H)-furanone), homofuronol (2-ethyl-5-methyl-4-hydroxy-3(2H)-furanone and 5-ethyl-2-methyl-4-hydroxy-3(2H)-furanone), maltol and derivatives (e.g. ethyl maltol), coumarin and derivatives, gamma-lactones (e.g. gamma-undecalactone, gamma-nonalactone), delta-lactones (e.g. 4-methyldelta-lactone, massoilactone, delta-decalactone, tuberolactone), methyl sorbate, divanillin, 4-hydroxy-2(or 5)-ethyl-5(or 2)-methyl-3(2H)furanone, 2-hydroxy-3-methyl-2-cyclopentenone, 3-hydroxy-4,5-dimethyl-2(5H)-furanone, fruit esters and fruit lactones (e.g. acetic acid n-butyl ester, acetic acid isoamyl ester, propionic acid ethyl ester, butyric acid ethyl ester, butyric acid n-butyl ester, butyric acid isoamyl ester, 3-methylbutyric acid ethyl ester, n-hexanoic acid ethyl ester, n-hexanoic acid allyl ester, n-hexanoic acid n-butyl ester, n-octanoic acid ethyl ester, ethyl 3-methyl-3-phenyl-glycidate, ethyl 2-trans-4-cis-decadienoate), 4-(p-hydroxyphenyl)-2-butanone, 1,1-dimethoxy-2,2,5-trimethyl-4-hexane, 2,6-dimethyl-5-hepten-1-al, 4-hydroxycinnamic acid, 4-methoxy-3-hydroxycinnamic acid, 3-methoxy-4-hydroxycinnamic acid, 2-hydroxycinnamic acid, 2,4-dihydroxybenzoic acid, 3-hydroxybenzoic acid, 3,4-dihydroxybenzoic acid, vanillic acid, homovanillic acid, vanillomandelic acid and phenylacetaldehyde.

Particular preference is given to flavorings which are able to positively influence the sweet taste without themselves exhibiting a strong sweetening action, such flavorings preferably being selected from the group consisting of: hesperetin according to WO 2007/014879 A1, hydroxyphenylalkadiones according to WO 2007/003527 A1, 4-hydroxychalcones according to WO 2007/107596 A1 and EP 1 972 203, propenylphenylglycosides (chavico-glycosides) according to EP 1 955 601 A1, phyllodulcin (or extracts containing phyllodulcin) according to EP 2 298 084, balansin A or balansin B (or extracts containing balansin A or B) according to WO 2012/164062, hydroxyflavanes according to EP 2 253 226, 1-(2,4-dihydroxyphenyl)-3-(3-hydroxy-4-methoxyphenyl)-propan-1-one according to EP 2 353 403, enzymatically treated rubusosides according to application number EP 14172306.4 or neoisoflavonoids according to EP 2 570 036.

Antioxidants

Both natural and synthetic antioxidants are used in the foodstuffs industry. Natural and synthetic antioxidants differ primarily in that the former occur naturally in foods and the latter are produced artificially. Natural antioxidants, as are to be used as food additives, are thus obtained, for example, from vegetable oils. Vitamin E—also known as tocopherol—is, for example, frequently produced from soybean oil. Synthetic antioxidants such as propyl gallate, octyl gallate and dodecyl gallate, on the other hand, are obtained by chemical synthesis. The gallates can cause allergies in sensitive people. Further antioxidants which can be used in compositions of the present invention are: sulfur dioxide, E 220 sulfites sodium sulfite, E 221 sodium hydrogen sulfite, E 222 sodium disulfite, E 223 potassium disulfite, E 224 calcium sulfite, E 226 calcium hydrogen sulfite, E 227 potassium hydrogen sulfite, E 228 lactic acid, E 270 ascorbic acid, E 300 sodium L-ascorbate, E 301 calcium L-ascorbate, E 302 ascorbic acid esters, E 304 tocopherol, E 306 alpha-tocopherol, E 307 gamma-tocopherol, E 308 delta-tocopherol, E 309 propyl gallate, E 310 octyl gallate, E 311 dodecyl gallate, E 312 isoascorbic acid, E 315 sodium isoascorbate, E 316 tert-butyl hydroquinone (TBHQ), E 319 butyl hydroxyanisole, E 320 butyl hydroxytoluene, E 321 lecithin, E 322 citric acid, E 330 salts of citric acid (E 331 & E 332) sodium citrate, E 331 calcium citrate, E 332 calcium disodium EDTA, E 385 diphosphates, E 450 disodium diphosphate, E 450a trisodium diphosphate, E 450b tetrasodium diphosphate, E 450c dipotassium diphosphate, E 450d tripotassium diphosphate, E 450e dicalcium diphosphate, E 450f calcium dihydrogen diphosphate, E 450g triphosphates, E 451 pentasodium triphosphate, E 451a pentapotassium triphosphate, E 451b polyphosphate, E 452 sodium polyphosphate, E 452a potassium polyphosphate, E 452b sodium calcium polyphosphate, E 452c calcium polyphosphate, E 452d tin(II) chloride, E 512.

Emulsifiers

Emulsifiers are distinguished by the important property of being soluble both in water and in fat. Emulsifiers mostly consist of a fat-soluble portion and a water-soluble portion. They are used whenever water and oil are to be made into a stable, homogeneous mixture. Suitable emulsifiers which are used in the foodstuffs-processing industry are selected from: ascorbyl palmitate (E 304) lecithin (E 322) phosphoric acid (E 338) sodium phosphate (E 339) potassium phosphate (E 340) calcium phosphate (E 341) magnesium orthophosphate (E 343) propylene glycol alginate (E 405) polyoxyethylene (8) stearate (E 430) polyoxyethylene stearate (E 431) ammonium phosphatides (E 442) sodium phosphate and potassium phosphate (E 450) sodium salts of fatty acids (E 470 a) mono- and di-glycerides of fatty acids (E 471) acetic acid monoglycerides (E 472 a) lactic acid monoglycerides (E 472 b) citric acid monoglycerides (E 472 c) tartaric acid monoglycerides (E 472 d) diacetyltartaric acid monoglycerides (E 472 e) sugar esters of fatty acids (E 473) sugar glycerides (E 474) polyglycerides of fatty acids (E 475) polyglycerol polyricinoleate (E 476) propylene glycol esters of fatty acids (E 477) sodium stearoyl lactylate (E 481) calcium stearoyl 2-lactylate (E 482) stearyl tartrate (E 483) sorbitan monostearate (E 491) stearic acid (E 570).

Food Colorings

Food colorings, or colorings for short, are foodstuff additives for coloring foodstuffs. Colorings are divided into the groups of natural colorings and synthetic colorings. Nature-identical colorings are likewise of synthetic origin. The nature-identical colorings are synthetic imitations of coloring substances which occur naturally. Suitable colorings for use in the present composition are selected from: curcumin, E 100 riboflavin, lactoflavin, laktoflavin, vitamin B2, E 101 tartrazine, E 102 Quinoline Yellow, E 104 Orange Yellow S, Orange Yellow RGL, E 110 cochineal, carminic acid, true carmine, E 120 azorubine, carmoisine, E 122 amaranth, E 123 Cochineal Red A, Ponceau 4 R, Brilliant Scarlet 4 R, E 124 erythrosine, E 127 Allura Red AC, E 129 Patent Blue V, E 131 indigotine, indigo carmine, E 132 Brilliant Blue FCF, Patent Blue AE, Amido Blue AE, E 133 chlorophylls, chlorophyllins, E 140 copper complexes of chlorophylls, copper-chlorophyllin complexes, E 141 Acid Brilliant Green, Green S, E 142 caramel color, E 150 a caustic sulfite caramel, E 150 b ammonia caramel, E 150 c sulfite ammonia caramel, E 150 d Brilliant Black FCF, Brilliant Black PN, Black PN, E 151 vegetable carbon, E 153 Brown FK, E 154 Brown HT, E 155 carotene, E 160 a annatto, bixin, norbixin, E 160 b capsanthin, capsorubin, E 160 c lycopene, E 160 d beta-apo-8'-carotenal, apocarotenal, beta-apocarotenal, E 160 e beta-apo-8'-carotenic acid ethyl ester (C30), apocarotene, beta-carotenic acid ester, E 160 f lutein, xanthophyll, E 161 b canthaxanthin, E 161 g betanin, beet red, E 162 anthocyanins, E 163 calcium carbonate, E 170 titanium dioxide, E 171 iron oxides, iron hydroxides, E 172 aluminum, E 173 silver, E 174 gold, E 175 Lithol Rubine BK, Pigment Rubine BK, E 180.

Cooling Active Ingredients

Suitable cooling active ingredients are, for example, menthol compounds which—in addition to the menthol basic structure itself—are selected, for example, from the group formed by menthol methyl ether, menthone glyceryl acetal (FEMA GRAS[1] 3807), menthone glyceryl ketal (FEMA GRAS 3808), menthyl lactate (FEMA GRAS 3748), menthol ethylene glycol carbonate (FEMA GRAS 3805), menthol propylene glycol carbonate (FEMA GRAS 3806), menthyl-N-ethyloxamate, monomethyl succinate (FEMA GRAS 3810), monomethyl glutamate (FEMA GRAS 4006), menthoxy-1,2-propanediol (FEMA GRAS 3784), menthoxy-2-methyl-1,2-propanediol (FEMA GRAS 3849) and the menthanecarboxylic acid esters and amides WS-3, WS-4, WS-5, WS-12, WS-14 and WS-30 and mixtures thereof.

[1] FEMA stands for "Flavor and Extracts Manufacturers Association" and GRAS is defined as "Generally Regarded As Safe". A substance labeled FEMA GRAS has been tested according to a standard method and is considered to be toxicologically safe.

A first important representative of these substances is monomethyl succinate (FEMA GRAS 3810). Both the succinate and the analogous monomethyl glutarate (FEMA GRAS 4006) are important representatives of monomethyl esters based on di- and poly-carboxylic acids:

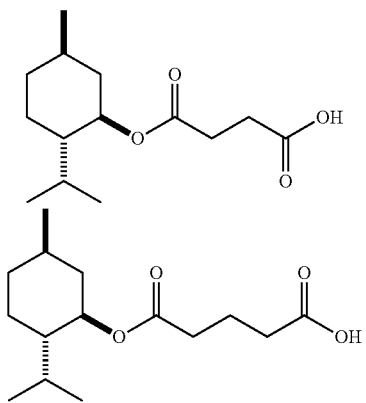

Examples of applications of these substances are to be found, for example, in publications WO 2003 043431 (Unilever) or EP 1332772 A1 (IFF).

The next important group of menthol compounds which are preferred within the meaning of the invention comprises carbonate esters of menthol and polyols, such as, for example, glycols, glycerol or carbohydrates, such as, for example, menthol ethylene glycol carbonate (FEMA GRAS 3805=Frescolat® MGC), menthol propylene glycol carbonate (FEMA GRAS 3784=Frescolat® MPC), menthol 2-methyl-1,2-propanediol carbonate (FEMA GRAS 3849) or the corresponding sugar derivatives. Likewise preferred are the menthol compounds menthyl lactate (FEMA GRAS 3748=Frescolat® ML) and in particular menthone glyceryl acetal (FEMA GRAS 3807) or menthone glyceryl ketal (FEMA GRAS 3808), which is marketed under the name Frescolat® MGA. Of these substances, menthone glyceryl acetal/ketal and menthyl lactate as well as menthol ethylene glycol carbonate and menthol propylene glycol carbonate, which are marketed by the applicant under the names Frescolat® MGA, Frescolat® ML, Frescolat® MGC and Frescolat® MPC, have been found to be most particularly advantageous.

In the 1970s, menthol compounds which have a C—C bond in the 3-position were developed for the first time, and a large number of representatives of these compounds can likewise be used. These substances are generally referred to as WS types. The basic structure is a menthol derivative in which the hydroxyl group has been replaced by a carboxyl group (WS-1). All further WS types, such as, for example, the preferred species WS-3, WS-4, WS-5, WS-12, WS-14 and WS-30, are derived from this structure.

INDUSTRIAL APPLICABILITY

A further aspect of the present invention relates to the use of homoeriodictyol (1), eriodictyol (2) and sterubin (4) in a foodstuff consumed for nourishment or pleasure, wherein homoeriodictyol (1), eriodictyol (2) and sterubin (4) are present in a concentration of 30 mg/kg, based on the total mass of the food. This use is preferably a non-therapeutic use for influencing the serotonin level and the concentration of free fatty acids in the blood in order to increase the appetite. Preference is likewise given to a use in which the foodstuff consumed for nourishment or pleasure is an orally consumable product.

A further subject of the invention relates to food supplements comprising
(i) at least one compound of formula (I) as claimed in claim 1 or salts thereof,
(ii) at least one solid carrier,
(iii) one or more flavorings,
with the proviso that the sum of components (i), (ii) and (iii), together with any further ingredients, is 100% by weight, based on the total amount of the total substance mixture.

The compounds of formula (I) are preferably selected from the group consisting of: homoeriodictyol (1), eriodictyol (2), hesperetin (3) and sterubin (4), wherein a food supplement according to the invention preferably comprises a mixture thereof, preferably mixtures of the (R) and/or (S) enantiomers, preferably a mixture of compounds of formula (I), preferably compounds (1) to (4), enriched in S configuration.

Advantageous carriers which may be mentioned are (preferably spray-dried) silicon dioxide (silica, silica gel), carbohydrates and/or carbohydrate polymers (polysaccharides), cyclodextrins, starches, degraded starches (starch hydrolyzates), chemically or physically modified starches, modified celluloses, gum arabic, ghatti gum, tragacanth, karaya gum, carrageenan, guar gum, locust bean gum, alginates, pectin, inulin or xanthan gum. Preferred starch hydrolyzates are maltodextrins and dextrins. Preferred carriers are silicon dioxide, gum arabic and maltodextrins, wherein maltodextrins having DE values in the range of from 5 to 20 are in turn preferred. It is not important which plant originally produced the starch for producing the starch hydrolyzates. Corn-based starches as well as starches from tapioca, rice, wheat or potatoes are suitable and readily available. The carriers can thereby also act as flow aids, such as, for example, silicon dioxide.

Encapsulation

Substance mixtures and preparations of the present invention which comprise hydroxyflavones of formula (I) can also be encapsulated if required. Encapsulation is usually carried out with the aid of solid coating materials, such as, for example, starches, including the degradation products thereof as well as chemically or physically produced derivatives (in particular dextrins and maltodextrins), gelatin, gum arabic, agar-agar, ghatti gum, gellan gum, modified and unmodified celluloses, pullulan, curdlan, carrageenans, alginic acid, alginates, pectin, inulin, xanthan gum and mixtures of two or more of these substances.

The solid encapsulating material is preferably a gelatin (in particular pork, beef, poultry and/or fish gelatin), wherein the gelatin preferably has a swelling factor of greater than or equal to 20, preferably of greater than or equal to 24. Likewise preferred are maltodextrins (in particular based on cereals, especially corn, wheat, tapioca or potatoes) which preferably have DE values in the range of from 10 to 20. Also preferred are celluloses (e.g. cellulose ethers), alginates (e.g. sodium alginate), carrageenan (e.g. beta-, iota-, lambda- and/or kappa-carrageenan), gum arabic, curdlan and/or agar agar.

Of these substances, gelatin is particularly preferred because it is readily available and can be acquired with different swelling factors. Most particularly preferred, in particular for oral applications, are seamless gelatin capsules or alginate capsules, the shell of which dissolves or disintegrates very quickly in the mouth or upon chewing. Corresponding capsules are described in detail, for example, in the following specifications EP 0389700 A1, U.S. Pat. Nos. 4,251,195, 6,214,376, WO 2003 055587 or WO 2004 050069 A1.

Alternatively, the capsules can also be microcapsules. The terms "microcapsule" or "nanocapsule" are understood by the person skilled in the art to mean spherical aggregates with a diameter in the range of from approximately 0.0001 to approximately 5 mm and preferably from 0.005 to 0.5 mm, which contain at least one solid or liquid core surrounded by at least one continuous shell. More precisely, they are finely dispersed liquid or solid phases encased in film-forming polymers, in the production of which the polymers, after emulsification and coacervation or interfacial polymerization, are deposited on the material to be encased. According to another method, molten waxes are taken up in a matrix ("microsponge") which as microparticles can additionally be encased in film-forming polymers. According to a third method, particles are alternately coated with polyelectrolytes having different charges ("layer-by-layer" method). The microscopically small capsules can be dried like powders. In addition to single-core microcapsules there are also known multi-core aggregates, also called microspheres, which contain two or more cores distributed in the continuous shell material. Single- or multi-core microcapsules can additionally be enclosed in an additional second, third etc. shell. The shell can be made of natural, semi-synthetic or synthetic materials. Natural shell materials are, for example, gum arabic, agar-agar, agarose, maltodextrins, alginic acid or its salts, for example sodium or calcium alginate, fats and fatty acids, cetyl alcohol, collagen, chitosan, lecithins, gelatins, albumin, shellac, polysaccharides, such as starches or dextran, polypeptides, protein hydrolyzates, sucrose and waxes. Semi-synthetic shell materials are inter alia chemically modified celluloses, in particular cellulose esters and ethers, for example cellulose acetate, ethylcellulose, hydroxypropylcellulose, hydroxypropylmethylcellulose and carboxymethylcellulose, as well as starch derivatives, in particular starch ethers and esters. Synthetic shell materials are, for example, polymers such as polyacrylates, polyamides, polyvinyl alcohol or polyvinylpyrrolidone.

Examples of microcapsules of the prior art are the following commercial products (the shell material is given in brackets in each case): Hallcrest Microcapsules (gelatin, gum arabic), Coletica Thalaspheres (marine collagen), Lipotec Millicapsules (alginic acid, agar-agar), Induchem Unispheres (lactose, microcrystalline cellulose, hydroxypropylmethylcellulose), Unicerin C30 (lactose, microcrystalline cellulose, hydroxypropylmethylcellulose), Kobo Glycospheres (modified starch, fatty acid esters, phospholipids), Softspheres (modified agar-agar) and Kuhs Probiol Nanospheres (phospholipids) as well as Primaspheres and Primasponges (chitosan, alginates) and Primasys (phospholipids).

Chitosan microcapsules and methods of producing them are well known from the prior art [WO 01/01926, WO 01/01927, WO 01/01928, WO 01/01929]. Microcapsules with mean diameters in the range of from 0.0001 to 5 mm, preferably from 0.001 to 0.5 mm and in particular from 0.005 to 0.1 mm, consisting of a shell membrane and a matrix containing the active ingredients, can be obtained, for example, by
(a) preparing a matrix from gel formers, cationic polymers and active ingredients,
(b) optionally dispersing the matrix in an oil phase,
(c) treating the dispersed matrix with aqueous solutions of anionic polymers and optionally thereby removing the oil phase.

Steps (a) and (c) can be interchanged if anionic polymers are used in step (a) instead of the cationic polymers and vice versa.

The capsules can also be produced by alternately encasing the active ingredient in layers of differently charged polyelectrolytes (layer-by-layer technology). Reference is made in this connection to European patent EP 1064088 B1 (Max-Planck Gesellschaft).

Substance mixtures and preparations of the present invention which comprise hydroxyflavones of formula (I) can also be produced, for example, by mechanical mixing operations, wherein the particles can also be comminuted at the same time, or by means of spray drying. Preference is given to compositions according to the invention which comprise solid carriers and are produced by means of spray drying; the particles so produced have a mean particle size in the range of from 30 to 300 μm and a residual moisture content of less than or equal to 5% by weight.

EXAMPLES

Example 1

Release of Serotonin in an Experimental Cell System with Homoeriodictyol

Human neuroblastoma cells (SH-SY5Y, ATCC number CRL-2266) are used as the cell model for the release of the neurotransmitter serotonin. Cultivation takes place at 37° C. and 5% $CO_2$ content with a mixture consisting of equal parts of Eagle's minimal essential medium (MEM) and F12 medium (in each case with 10% FBS and 1 penicillin/ streptomycin). For measurement of the serotonin release, the cells are harvested with trypsin and, after a vitality test by trypan blue staining, sown in 35 mm cell culture dishes in a defined cell number.

After stimulation of $1.25*10^6$ human neuroblastoma cells (SH-SY5Y) for 5 minutes with 300 μl of Krebs-Ringer-HEPES buffer, 0.1% ascorbic acid, pH 6.2, with or without addition of the homoeriodictyol, wherein concentrations of 0.001 μM, 0.01 μM, 0.1 μM, 1 μM and 10 μM in the Krebs-Ringer-HEPES buffer are established when the homoeriodictyol is added, the serotonin content is determined by means of an enzyme-based detection method (Serotonin-ELISA sensitive, DLD Diagnostica, Hamburg, Germany). The cells are lyzed with a buffer containing sodium lauroyl sarcosinate and the DNA content is determined by means of a NanoQuant plate (Tecan, Ménnendorf, Switzerland) for normalization of the serotonin release. The results are summarized in Table 1.

TABLE 1

Serotonin release SH-SY5Y cells after stimulation with homoeriodictyol

| Test substance | T/C [%] | Standard deviation [%] |
|---|---|---|
| Control (with 0.1% EtOH) | 100 | 14.0 |
| Homoeriodictyol 0.001 μM | 62.2 | 23.4 |

TABLE 1-continued

Serotonin release SH-SY5Y cells after stimulation with homoeriodictyol

| Test substance | T/C [%] | Standard deviation [%] |
|---|---|---|
| Homoeriodictyol 0.01 μM | 42.9 | 13.3 |
| Homoeriodictyol 0.1 μM | 42.6 | 11.5 |
| Homoeriodictyol 1 μM | 43.5 | 21.1 |
| Homoeriodictyol 10 μM | 71.9 | 22.3 |

FIG. 1 shows the serotonin release from neuronal SH-SY5Y cells after incubation with homoeriodictyol in concentrations of 0.001 μM, 0.01 μM, 0.01 μM, 1 μM and 10 μM. The results are shown in % relative to the control (buffer with 0.1% ethanol). n=3, tR=2. Significant differences in the treatments relative to the control were tested with a single-factor ANOVA with a subsequent Holm-Sidak post hoc test against the control and marked according to the following scheme: * $p \leq 0.05$;  $p \leq 0.01$; * $p \leq 0.001$. Concentration-dependent differences were tested with a single-factor ANOVA with a subsequent Holm-Sidak post hoc test and identified by different letters (a, b), wherein no common letter marks a significant difference.

Example 2

Change in the Serotonin Plasma Concentration of Healthy Subjects after Administration of 125 ml of Water (Control) or 30 mg of Homoeriodictyol Dissolved in 125 ml of Water In order to determine the serotonin plasma concentration, whole blood is taken from healthy subjects in each case on a test day before and on average 37 minutes after administration of the test solution (1st test day: 125 ml of water; 2nd test day: 30 mg of homoeriodictyol dissolved in 125 ml of water).

The plasma is obtained from the whole blood by refrigerated centrifugation for 15 minutes at 1800×g, and the serotonin concentration in the plasma is determined by an enzyme-based detection method (Serotonin ELISA, DLD Diagnostika, Germany).

The change in the serotonin plasma concentration before and after administration of 125 ml of water or 30 mg of homoeriodictyol dissolved in 125 ml of water is shown in Table 2. There is a significant difference between the two treatments (p<0.05; n=10), which was determined by a dependent, two-sided Student's T-test and is marked *. The results are summarized in Table 2.

TABLE 2

Change in the serotonin plasma concentration by addition of water and homoeriodictyol

| | 125 ml of water | 30 mg of homoeriodictyol in 125 ml of water |
|---|---|---|
| Change in the serotonin concentration in the plasma after administration of the test solution | −6.81 ± 10.6 | −19.1 ± 10.6* |

Figure 2:
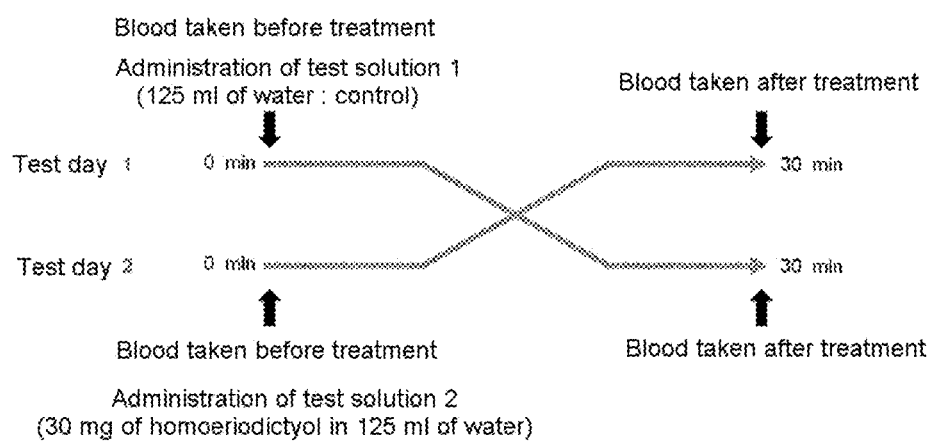

FIG. 2 shows a schematic representation of the test procedure of the crossover human intervention for determining the change in the serotonin plasma concentration 30 minutes after administration of 125 ml of water (test day 1) or 30 mg of homoeriodictyol dissolved in 125 ml of water (test day 2).

Example 3

Reduction of the Absolute Plasma Serotonin Concentration after Oral Administration of 30 mg of Homoeriodictyol In order to determine the serotonin plasma concentration, whole blood is taken from healthy subjects on a test day before and on average 35 minutes after administration of 30 mg of homoeriodictyol dissolved in 125 ml of water. The plasma is obtained from the whole blood by refrigerated centrifugation for 15 minutes at 1800×g, and the serotonin concentration in the plasma is determined by an enzyme-based detection method (Serotonin-ELISA, DLD Diagnostika, Germany).

The change in the serotonin plasma concentration before and after administration of 30 mg of homoeriodictyol dissolved in 125 ml of water is shown in Table 3. There is a significant difference between the two treatments (p<0.05, n=16), which was determined by a dependent, two-sided Student's T-test and is marked *. The results are summarized in Table 3.

TABLE 3

Change in the serotonin plasma concentration by addition of water and homoeriodictyol

|  | Before oral administration of 30 mg of homoeriodictyol in 125 ml of water | After oral administration of 30 mg of homoeriodictyol in 125 ml of water |
| --- | --- | --- |
| Serotonin concentration in the plasma [nmol] | 306 ± 152 | 192 ± 122* |

Figure 3:
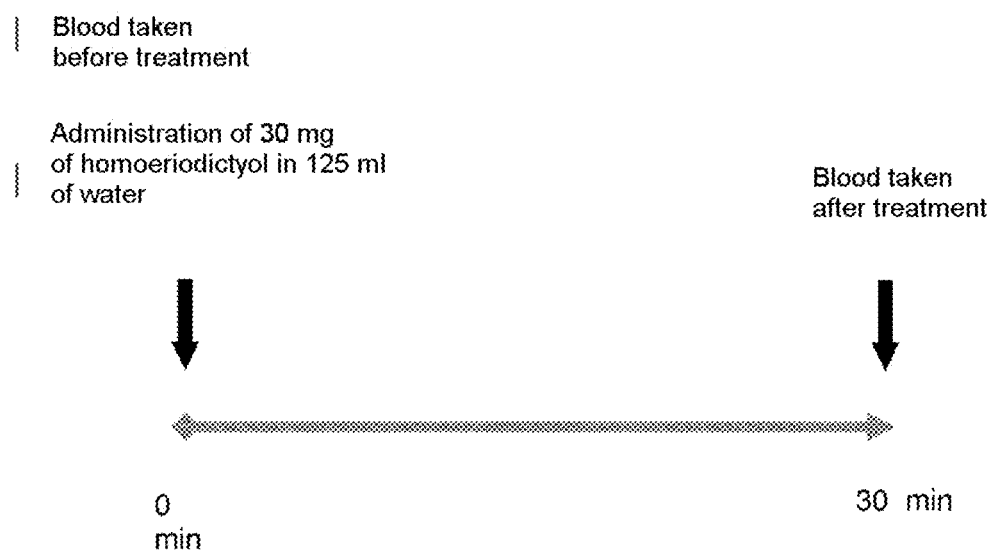
FIG. 3 is a schematic representation of the test procedure for determining the absolute plasma serotonin concentration after oral administration of 30 mg of homoeriodictyol dissolved in 125 ml of water in accordance with aspects of the disclosure.

FIG. 3 shows a schematic representation of the test procedure for determining the absolute plasma serotonin concentration after oral administration of 30 mg of homoeriodictyol dissolved in 125 ml of water.

Example 4

Fatty Acid Uptake in an Experimental Test System with Homoeriodictyol

3T3-L1 preadipocytes (ATCC CL-173) are used as the cell model for the uptake of free fatty acid into peripheral cells, here adipocytes. Cultivation is carried out at 37° C. and 5% $CO_2$ content in DMEM culture medium to which 10% FBS 4% L-glutamine and 1% penicillin/streptomycin have been added. In order to measure the fatty acid uptake, the 3T3-L1 cells are differentiated in 175 $cm^2$ cell culture bottles from fully matured adipocytes. To that end, two days after reaching confluence, the cells are stimulated to differentiate for 48 hours by the addition of 10 μg/ml insulin, 1 μM dexamethasone and 0.5 mM isobutyl methyl xanthine from the culture medium. After the cells have been treated for a further 48 hours with 10 μg/ml insulin in the cell culture medium, normal culture medium is again used until the adipocytes are fully mature. The cells are usually used for the test seven to nine days after the onset of differentiation. To that end, the cells are harvested with trypsin and, after a positive vitality test with trypan blue, scattered in a 96-well plate at a rate of 65,000 cells per well.

Measurement of the fatty acid uptake is carried out after a 60-minute synchronization of the cells by removal of the fetal bovine serum and a 30-minute preincubation with Hank's balanced salt solution, to which 20 mM HEPES (HBSS/HEPES), with or without the addition of from 0.01 to 10 μM of homoeriodictyol, by means of a fluorescence-labeled fatty acid analog (QBT Fatty Acid Uptake kit, Molecular Devices, Germany), have been added. The change in the area under the curve formed by the increase in the fluorescence signal over the course of one hour is shown in % in comparison with the control.

The change in the fatty acid uptake in 3T3-L1 adipocytes after preincubation for 30 minutes with HESS/HEPES buffer with 0.1% ethanol (control) or 0.01-10 μM homoeriodictyol dissolved in HBSS/HEPES buffer is shown in Table 4. Significant differences (p<0.001) relative to the control were tested with a single-factor ANOVA against the control with a subsequent Dunn's post hoc test and are marked ***. Mean values from 3-4 independent experiments with in each case 3 repetitions are shown. The results are summarized in Table 4.

TABLE 4

Change in fatty acid uptake by addition of homoeriodictyol

| Test substance | Change in % | Standard deviation [%] |
| --- | --- | --- |
| EtOH control | 0 | 4.48 |
| Homoeriodictyol 0.01 μM | 4.34 | 6.80 |
| Homoeriodictyol 0.1 μM | 8.78*** | 8.05 |
| Homoeriodictyol 1 μM | 4.10 | 3.16 |
| Homoeriodictyol 10 μM | −0.47 | 6.67 |

Figure 4:
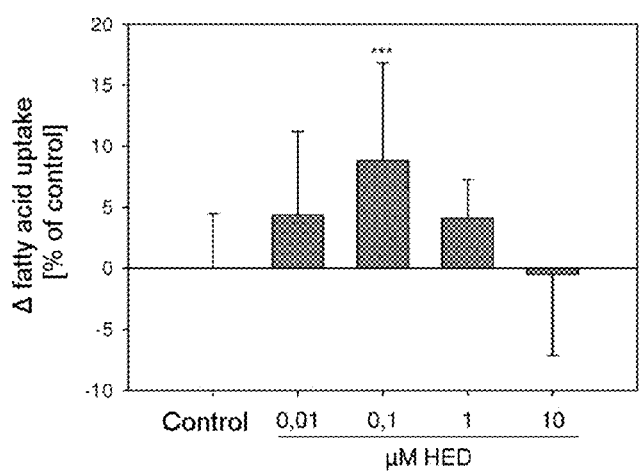
FIG. 4 is a graph showing the change in the fatty acid uptake in 3T3-L1 adipocytes after preincubation for 30 minutes with HBSS/HEPES buffer with 0.1% ethanol (control) or 0.01-10 µM homoeriodictyol dissolved in HBSS/HEPES buffer according to the aspects of the disclosure.

The change in the fatty acid uptake in 3T3-L1 adipocytes after preincubation for 30 minutes with HBSS/HEPES buffer with 0.1% ethanol (control) or 0.01-10 μM homoeriodictyol dissolved in HBSS/HEPES buffer is shown in FIG. 4. Significant differences (p<0.001) relative to the control were tested with a single-factor ANOVA against the control with a subsequent Dunn's post hoc test and are marked ***. Mean values from 3-4 independent experiments with in each case 3 repetitions are shown.

Example 5

Plasma Concentration of Homoeriodictyol after Oral Administration of Homoeriodictyol to Healthy Test Persons The plasma concentration after oral ingestion of 30 mg of homoeriodictyol, dissolved in 125 ml of water, was studied by taking 4 ml of whole blood in EDTA Monovettes (Sarstedt, Germany), before and 30 minutes after administration of the homoeriodictyol test solution. The plasma is obtained from the whole blood by refrigerated centrifugation for 15 minutes at 1800×g. The homoeriodictyol in the plasma is purified by a solid-phase extraction, and the concentration is determined by LC-MS with internal calibration via eriodictyol.

The homoeriodictyol plasma concentration of seven healthy test persons 30 minutes after oral administration of 30 mg of HED is shown in Table 5. The mean value was formed from n=7. The concentration range tested in vitro (Examples 1 and 4) accordingly corresponds to the plasma concentration 30 minutes after oral administration of 30 mg of homoeriodictyol.

TABLE 5

Homoeriodictyol plasma concentration of test persons after oral administration of 30 mg of HED

|  | Lowest concentration [µM] | Maximum concentration [µM] | Mean value ± standard deviation [µM] |
|---|---|---|---|
| Homoeriodictyol in the plasma | 0.01 | 0.08 | 0.04 ± 0.02 |

APPLICATION EXAMPLES A-E

Example A

Refreshment Drinks (Sugar-Containing, Reduced-Calorie, Calorie-Free)

The ingredients were mixed in the indicated order and made up to 100% in water. The mixtures are introduced into glass bottles and carbonized.

| Ingredient Preparation | I | II | III | IV | V | VI | VII |
|---|---|---|---|---|---|---|---|
| Sugar (sucrose) | 10 | 10 | 7 | — | — | 8 | 7 |
| Glucose/fructose syrup from corn, containing 55% by weight fructose | — | — | — | — | 10 | — | — |
| Rebaudioside A 95% | — | — | 0.02 | 0.05 | — | — | — |
| Citric acid | 0.15 | 0.15 | 0.06 | 0.15 | 0.15 | 0.15 | 0.15 |
| Phosphoric acid | — | — | 0.07 | — | — | — | — |
| Caramel color | — | — | 0.14 | — | — | — | — |
| Caffeine | — | — | 0.01 | — | — | — | — |
| Lemon flavoring | 0.1 | 0.05 | — | 0.1 | 0.1 | 0.1 | 0.1 |
| Limonene flavoring | — | 0.05 | — | — | — | — | — |
| "Cola"-type drink emulsion | — | — | 0.05 | — | — | — | — |
| Phloretin | — | — | 0.002 | 0.003 | — | 0.002 | 0.001 |
| Hesperetin | — | — | 0.001 | 0.002 | — | — | 0.002 |
| Extract from *Rubus suavissimus*, containing 5% by weight rubusoside, based on the total weight of the extract | — | — | — | — | — | 0.01 | — |
| Homoeriodictyol sodium salt | — | — | 0.010 | 0.005 | — | — | — |
| Water | | | make up to 100 | | | | |

Example B

Use in a Chewing Gum

Parts A to D are mixed and kneaded intensively. The crude mass can be processed, for example, in the form of thin strips to form ready-to-eat chewing gums; all amounts given in % by weight.

| PART | Ingredient | VIII | IX |
|---|---|---|---|
| A | Chewing gum base, "Jagum T" | Make up to 100 | Make up to 100 |
| B | Sorbitol, powdered | 39.00 | 39.00 |
|  | Isomalt ® (Palatinit GmbH) | 9.50 | 9.50 |
|  | Xylitol | 2.00 | 2.00 |
|  | Mannitol | 3.00 | 3.00 |
|  | Aspartame ® | 0.10 | 0.10 |
|  | Acesulfame ® K | 0.10 | 0.10 |
|  | Emulgum ® (Colloides Naturels, Inc.) | 0.30 | 0.30 |
| C | Sorbitol, 70% | 14.00 | 14.00 |
|  | Glycerol | 1.00 | 1.00 |
| D | Peppermint flavoring | 0.5 | 0.5 |
|  | Homoeriodictyol sodium salt | 0.03 | 0.01 |
|  | Eriodictyol | 0.0100 | — |

Example C

Use in Hard Caramels

Palatinit or the sugar were mixed with water, where appropriate after addition of the citric acid, and the mixture was melted at 165° C. and then cooled to 115° C. The flavoring and the other constituents were added and, after being thoroughly mixed, the mixture was poured into molds, removed from the molds after solidifying and then packed individually.

| Ingredients | X | XI | XII | XIII |
|---|---|---|---|---|
| Sugar | 74.50 | — | — | — |
| Palatinit, type M | — | 74.00 | 75.50 | 75.00 |
| Citric acid | 0.5 | 1.0 | 0.5 | — |
| Coloring yellow | — | 0.01 | — | — |
| Coloring red | — | — | 0.01 | — |
| Coloring blue | 0.01 | — | — | 0.01 |
| Peppermint flavoring | 0.1 | — | — | 0.1 |
| Lemon flavoring | — | 0.1 | — | — |
| Red fruit flavoring | — | — | 0.1 | — |
| Rebaudioside A 98% | — | 0.040 | — | 0.040 |
| Balansin A according to [SY317] | — | 0.005 | 0.010 | 0.005 |
| Hesperetin | — | 0.001 | — | 0.001 |
| Phloretin | — | 0.002 | — | — |
| Homoeriodictyol sodium salt | 0.02 | 0.001 | 0.002 | 0.02 |
| Water | ad 100 | ad 100 | ad 100 | ad 100 |

Example D

Low-Fat Yoghurt

The ingredients were mixed and cooled to 5° C.; all amounts given as % by weight.

| Ingredient | XIV | XV | XVI | XVII |
|---|---|---|---|---|
| Sucrose | 10 | 8 | 6 | — |
| Rebaudioside A 98% | — | — | — | 0.050 |
| Extract from *Rubus suavissimus*, containing 5% by weight rubusoside, based on the total weight of the extract, for example of plant extract | — | 0.010 | 0.010 | — |
| Hesperetin | — | 0.001 | 0.001 | 0.002 |
| Phloretin | — | — | 0.002 | 0.002 |

-continued

| Ingredient | XIV | XV | XVI | XVII |
|---|---|---|---|---|
| Homoeriodictyol sodium salt | 0.003 | 0.010 | 0.002 | 0.005 |
| Yoghurt, 0.1% fat | | make up to 100% | | |

Example E

Fruit Gum

Polydextrose is a non-sweet-tasting polysaccharide with a low energy value; all amounts given as % by weight.

| Ingredients | XVIII | XIX |
|---|---|---|
| Sucrose | 34.50 | 8.20 |
| Glucose syrup, DE 40 | 31.89 | 30.09 |
| Iso Syrup C* Tru Sweet 01750 (Cerestar GmbH) | 1.50 | 2.10 |
| Gelatin 240 bloom | 8.20 | 9.40 |
| Polydextrose (Litesse ® Ultra, Danisco Cultor GmbH) | — | 24.40 |
| Yellow and red coloring | 0.01 | 0.01 |
| Citric acid | 0.20 | |
| Cherry flavoring, containing 1% by weight homoeriodictyol and 0.3% by weight hesperetin, based on the flavoring | 0.20 | 0.10 |
| Water | ad 100 | ad 100 |

The invention claimed is:

1. A method for reducing serotonin levels in a mammal in need thereof comprising orally administering to the mammal a dose of about 0.03 µg/kg to about 3 mg/kg of a compound selected from the group consisting of:

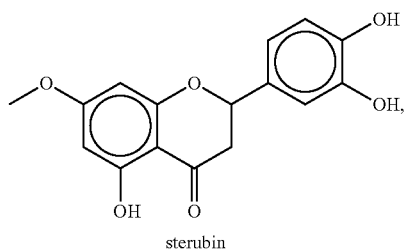

homoeriodictyol

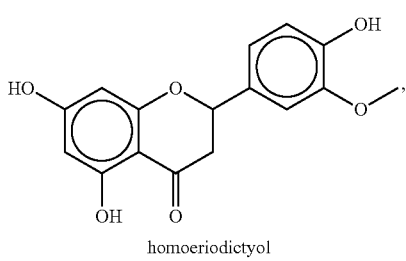

eriodictyol

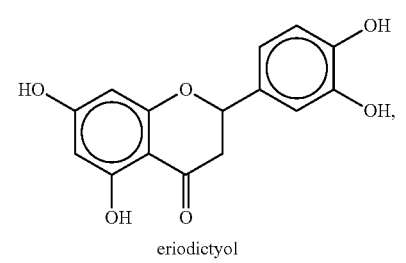

hesperetin, and

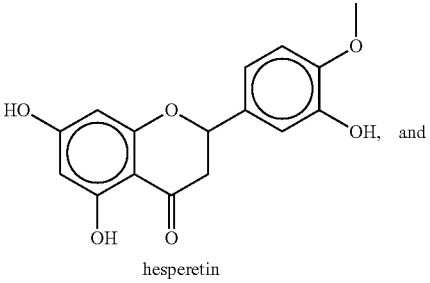

sterubin a salt thereof, and mixtures thereof.

2. The method of claim 1, wherein the compound is administered as an orally consumable medicament.

3. The method of claim 2, wherein the orally consumable medicament comprises:

(i) at least one compound selected from the group consisting of:

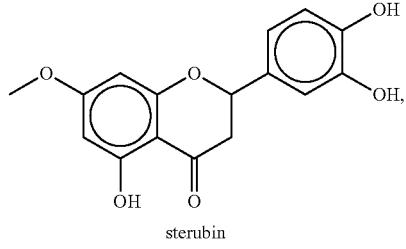

homoeriodictyol

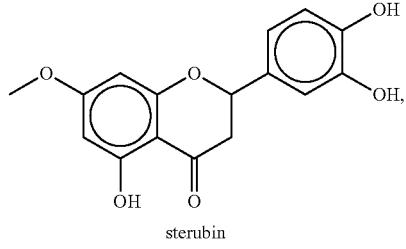

eriodictyol

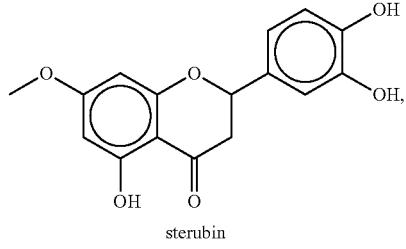

hesperetin, and

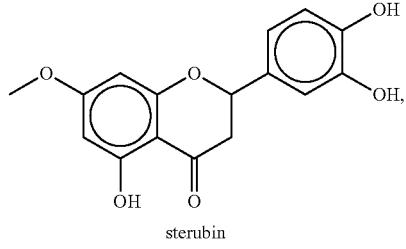

sterubin a salt thereof, and mixtures thereof, (ii) at least one solid carrier, and
(iii) one or more flavorings,
with the proviso that the sum of components (i), (ii) and (iii), together with any further ingredients, is 100% by weight, based on the total amount of the medicament.

4. The method of claim 1, wherein countercations of the salts are selected from the group consisting of ammonium, trialkylammonium, sodium, potassium, magnesium, calcium, and mixtures thereof.

5. The method of claim 1, wherein the compound is administered as an orally consumable foodstuff consumed for nourishment or pleasure comprising:
(i) at least one compound selected from the group consisting of:

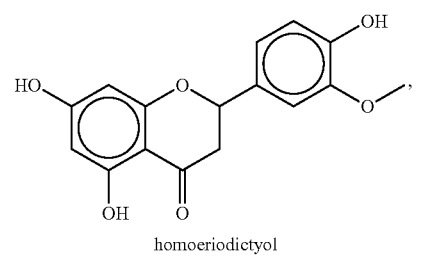
homoeriodictyol

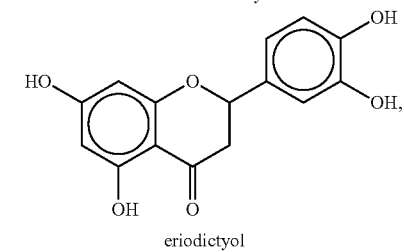
eriodictyol

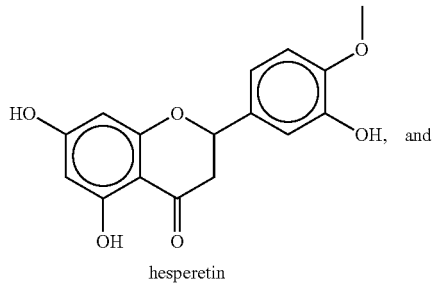
hesperetin

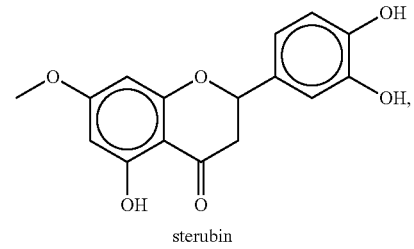
sterubin a salt thereof, and a mixture thereof,
(ii) at least one solid carrier, and
(iii) one or more flavorings,
with the proviso that the sum of components (i), (ii) and (iii), together with any further ingredients, is 100% by weight, based on the total amount of the foodstuff.

6. The method of claim 1, wherein the compound is administered as a food supplement comprising:
(i) at least one compound selected from the group consisting of:

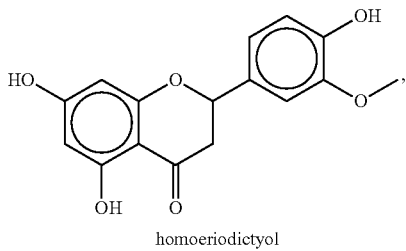
homoeriodictyol

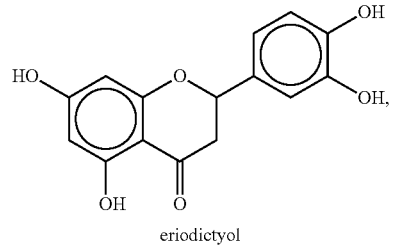
eriodictyol

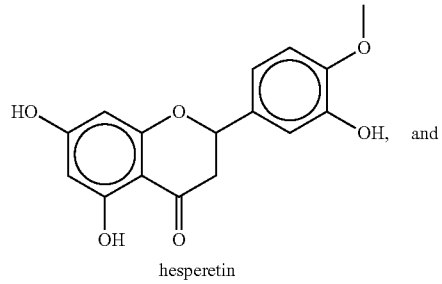
hesperetin

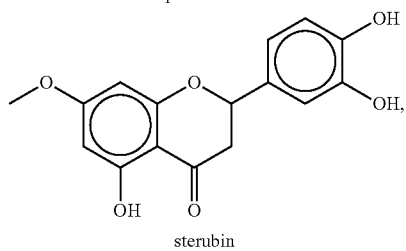
sterubin a salt thereof, and mixtures thereof,
(ii) at least one solid carrier, and
(iii) one or more flavorings,
with the proviso that the sum of components (i), (ii) and (iii), together with any further ingredients, is 100% by weight, based on the total amount of the food supplement.

7. The method of claim 2, wherein the medicament is a tablet or capsule.

8. The method of claim 3, wherein the at least one solid carrier is selected from silicone dioxide, gum Arabic, and a maltodextrin having a DE value in the range of 5 to 20.

9. The method of claim 3, wherein the at least one solid carrier has a mean particle size of 30 to 300 mm and a residual moisture content of less than or equal to 5% by weight.

10. The method of claim 5, wherein the at least one solid carrier is selected from silicone dioxide, gum Arabic, and a maltodextrin having a DE value in the range of 5 to 20.

11. The method of claim 5, wherein the at least one solid carrier has a mean particle size of 30 to 300 μm and a residual moisture content of less than or equal to 5% by weight.

12. The method of claim 5, wherein the foodstuff further comprises:

(iv) one or more sweeteners.

13. The method of claim 12, wherein the foodstuff further comprises:

(v) one or more thickeners.

14. The method of claim 5, wherein the foodstuff is chewing gum comprising a water-insoluble component and a water-soluble component.

* * * * *